(12) United States Patent
Hewlett et al.

(10) Patent No.: US 11,796,784 B2
(45) Date of Patent: Oct. 24, 2023

(54) SURGICAL MICROSCOPE SYSTEM

(71) Applicants: Robert T. Hewlett, Cumming, GA (US); Jonathan M. Butler, Gainesville, GA (US)

(72) Inventors: Robert T. Hewlett, Cumming, GA (US); Jonathan M. Butler, Gainesville, GA (US)

( * ) Notice: Subject to any disclaimer, the term of this patent is extended or adjusted under 35 U.S.C. 154(b) by 0 days.

(21) Appl. No.: 17/985,344

(22) Filed: Nov. 11, 2022

(65) Prior Publication Data

US 2023/0152567 A1 May 18, 2023

Related U.S. Application Data

(60) Provisional application No. 63/347,131, filed on May 31, 2022, provisional application No. 63/278,691, filed on Nov. 12, 2021.

(51) Int. Cl.
| | |
|---|---|
| *G02B 21/06* | (2006.01) |
| *G02B 21/00* | (2006.01) |
| *A61B 90/30* | (2016.01) |
| *A61F 9/007* | (2006.01) |

(52) U.S. Cl.
CPC .............. *G02B 21/06* (2013.01); *A61B 90/30* (2016.02); *A61F 9/007* (2013.01); *G02B 21/0012* (2013.01)

(58) Field of Classification Search
CPC .... G02B 21/06; G02B 21/0012; G02B 21/00; A61B 90/30; A61F 9/007
See application file for complete search history.

(56) References Cited

U.S. PATENT DOCUMENTS

| | | | | |
|---|---|---|---|---|
| 5,982,532 A | * | 11/1999 | Mittelstadt | ......... G02B 21/0012 359/368 |
| 8,205,988 B2 | | 6/2012 | Fujii et al. | |
| 9,662,013 B2 | | 5/2017 | Fukuma et al. | |
| 2002/0030823 A1 | * | 3/2002 | Kobayashi | ............. G01B 11/06 356/485 |
| 2003/0142861 A1 | * | 7/2003 | Penkethman | ...... G01R 31/2891 382/151 |

(Continued)

FOREIGN PATENT DOCUMENTS

| | | | | |
|---|---|---|---|---|
| CN | 107111046 A | * | 8/2017 | ......... G02B 19/0066 |
| CN | 112493982 A | | 3/2021 | |
| WO | WO2020/084611 A1 | | 4/2020 | |

OTHER PUBLICATIONS

Notification of Transmittal and the International Search Report and Written Opinion of the International Searching Authority for PCT/US22/49696 dated Mar. 31, 2023.

*Primary Examiner* — Mustak Choudhury
(74) *Attorney, Agent, or Firm* — Womble Bond Dickinson (US) LLP

(57) ABSTRACT

A surgical microscope system having a head unit microscope assembly and a foot control assembly in operative communication with the head unit microscope assembly. The head unit microscope assembly being configured to selectively couple to a floor stand assembly such that the that the head unit microscope assembly can be positioned in a desired operative location by the user. The head unit microscope assembly including one or more of: a mounting adaptor, an XY directional stage, a tilt drive, a focus drive; a microscope subassembly, and/or an illumination system.

31 Claims, 35 Drawing Sheets

(56) References Cited

U.S. PATENT DOCUMENTS

| | | | |
|---|---|---|---|
| 2004/0034534 A1* | 2/2004 | Sander | A61B 90/20 704/275 |
| 2005/0277913 A1* | 12/2005 | McGary | G02B 27/01 606/1 |
| 2008/0021711 A1* | 1/2008 | Claus | G16H 20/40 704/275 |
| 2014/0121468 A1* | 5/2014 | Eichenholz | A61B 1/0638 600/249 |
| 2015/0378142 A1* | 12/2015 | Reimer | G02B 21/082 359/385 |
| 2016/0154193 A1* | 6/2016 | Brukilacchio | G02B 19/0066 385/33 |
| 2018/0307023 A1* | 10/2018 | Jess | G02B 23/2484 |
| 2019/0201161 A1* | 7/2019 | Yu | A61B 90/50 |
| 2020/0214555 A1 | 7/2020 | Fukuma et al. | |

* cited by examiner

SURGICAL MICROSCOPE SYSTEM

CROSS REFERENCE

The present Patent Application claims benefit of U.S. Provisional Patent Application No. 63/278,691 filed Nov. 12, 2021, and claims benefit of U.S. Provisional Patent Application No. 63/347,131, filed May 31, 2022.

INCORPORATION BY REFERENCE

U.S. Provisional Patent Application No. 63/278,691, filed Nov. 12, 2021, and U.S. Provisional Patent Application No. 63/347,131, filed May 31, 2022, are specifically incorporated by reference herein as if set forth in their entireties.

TECHNICAL FIELD

The present disclosure relates generally to systems, apparatus and methods in the field of surgical microscopes, more particularly, to various aspects involving systems, apparatus and methods for improved microscope assisted surgical outcomes using a microscope system that utilizes single spot, diverging, coaxial illumination.

BACKGROUND

As one will appreciate, any microsurgical procedure requires precision cutting and/or removal of various body tissues. For example, in ophthalmic microsurgical procedures, inner limiting membrane (ILM) removal and epiretinal membrane (ERM) removal are exemplary surgical treatments for different macular surface diseases. However, the surgical techniques for ILM and ERM removal require skill and patience. In the ophthalmic context and in other microscopic surgical contexts, precise and carefully constructed surgical instruments are used for each aspect of the surgical technique to ensure a successful outcome for the patient.

To aid the operator with various microsurgical procedures, operators may use an imaging system that presents a microscope subject view of the tissue to be treated, such as a view of the tissue of the patient's eye. In an exemplary ophthalmic surgery context, the user of such an imaging system may be provided with a close-up view of the surgical instruments, such as forceps or other tools, as well as the region of the eye that is of interest. In some cases, the operator may also be provided with additional information that may be useful to the operator in an overlaid display, visible through the eyepieces of the microscope.

In ophthalmic devices and ophthalmic microsurgical procedures, reflections of light sources can be seen in the image of the eye. As a result, important information about the condition or existing changes in the eye can be outshined, covered and/or changed. Alternatively, the light sources used with surgical microscopes to illuminate the surgical field in the patient's eye are conventionally focused and resultantly reach light intensities that are painful to the patient and that persists throughout the surgical procedure.

Accordingly, there is a need for continued improvement in the use and operability of microsurgical systems for microscope-assisted procedures. There is a particular need for improvement in the use and operability of microsurgical systems various ophthalmic procedures where it is desirable to enhance the clarity of the microscopic view of the targeted tissues and to minimize patient surgical procedure pain, which are caused by the light source of the surgical microscope system.

SUMMARY

To improve the state of the art, disclosed herein is a surgical microscope system, and methods of use thereof, utilizing novel features and functionalities. The surgical microscope system can include at least one of: a head unit microscope assembly; a foot control assembly in operative communication with the head unit microscope assembly; a floor stand configured to support the head unit microscope assembly in a desired operative position; a remote viewing assembly in operative communication with the head unit microscope assembly; and a head rest assembly that allows a surgeon to rest their head into a custom fit support device in order to alleviate strain on the surgeon's neck and upper back muscles by allowing the surgeon to rest the weight of his/her head against the face piece during surgery.

In one aspect, the head unit microscope assembly can have a mounting adaptor that is configured to operatively couple to any existing surgical microscope floor stand, regardless of brand, which allows for upgrade of a surgical microscope's optical portion to provide functions and benefits that are not currently available in dated prior existing surgical microscopes. In a further aspect, the head unit microscope assembly is configured to house the head unit movement subassembly and the control system for the surgical microscope system. Thus, in one aspect, it is contemplated that the presented head unit microscope assembly can be configured to be self-contained, i.e., all of the mechanical; electronic controls, computer systems, programing, etc. necessary for operation of the head unit microscope assembly is formed as a portion of the head unit microscope assembly. Optionally, if the floor stand that the head unit microscope assembly is retrofitted thereto contains operational electronics, the head unit microscope assembly can be configured to selectively communicate with the floor stand electronics.

The foot control assembly can operate as the primary control interface for the head unit microscope assembly. In one aspect, the foot control assembly can comprise a wireless, battery operated device that is configured to reduce cord clutter in an operating room and can further have control switches that are positioned in a conventional surgical control layout. In this aspect, it is contemplated that the control switches for the foot control assembly can comprise at least one of uses hall effect (magnetic) and/or optical switches for increased surgical reliability.

The floor stand assembly can be optionally used if the user does not have a current upgradable floor stand or wants added features that are provided by the floor stand assembly. The floor stand assembly is configured to be light weight, when compared to existing surgical operating microscopes, which allows for easier movement of the floor stand and the coupled head unit microscope assembly by the user. To stabilize the floor stand assembly, the floor stand is configured to accept the mounting of conventional weight plates, which allows the selective addition of the required ballast to insure the desired positional stability of the surgical microscope system.

The remote viewing assembly is in operative communication with the head unit microscope assembly and can comprise an opposed pair of high resolution cameras that are configured to produce a left and right view of the image in the microscope, which are subsequently combined and displayed on a remote 3D monitor. A user can use passive 3D glasses to perceive the displayed 3D image. Alternatively, the remote viewing assembly is configured to allow for the user to use the conventional binocular view of the microscope to view the image concurrently with the view of the image being presented on the remote 3D monitor.

The headrest assembly is attachable to the head unit microscope assembly and is configured to support the head, neck and back of a user who leans against it, and the invention provides a selectable position against which the user may lean in order to prevent neck and back strain.

Still other aspects, embodiments, and advantages of these exemplary aspects and embodiments, are discussed in detail below. Moreover, it is to be understood that both the foregoing information and the following detailed description are merely illustrative examples of various aspects and embodiments, and are intended to provide an overview or framework for understanding the nature and character of the claimed aspects and embodiments. Accordingly, these and other objects, along with advantages and features of the present invention herein disclosed, will become apparent through reference to the following description and the accompanying drawings. Furthermore, it is to be understood that the features of the various embodiments described herein are not mutually exclusive and can exist in various combinations and permutations.

BRIEF DESCRIPTION OF THE DRAWINGS

The accompanying drawings, which are included to provide a further understanding of the embodiments of the present disclosure, are incorporated in and constitute a part of this specification, illustrate embodiments of the present disclosure, and together with the detailed description, serve to explain the principles of the embodiments discussed herein. No attempt is made to show structural details of this disclosure in more detail than can be necessary for a fundamental understanding of the exemplary embodiments discussed herein and the various ways in which they can be practiced. According to common practice, the various features of the drawings discussed below are not necessarily drawn to scale. Dimensions of various features and elements in the drawings can be expanded or reduced to more clearly illustrate the embodiments of the disclosure.

DETAILED DESCRIPTION

Figure 1:
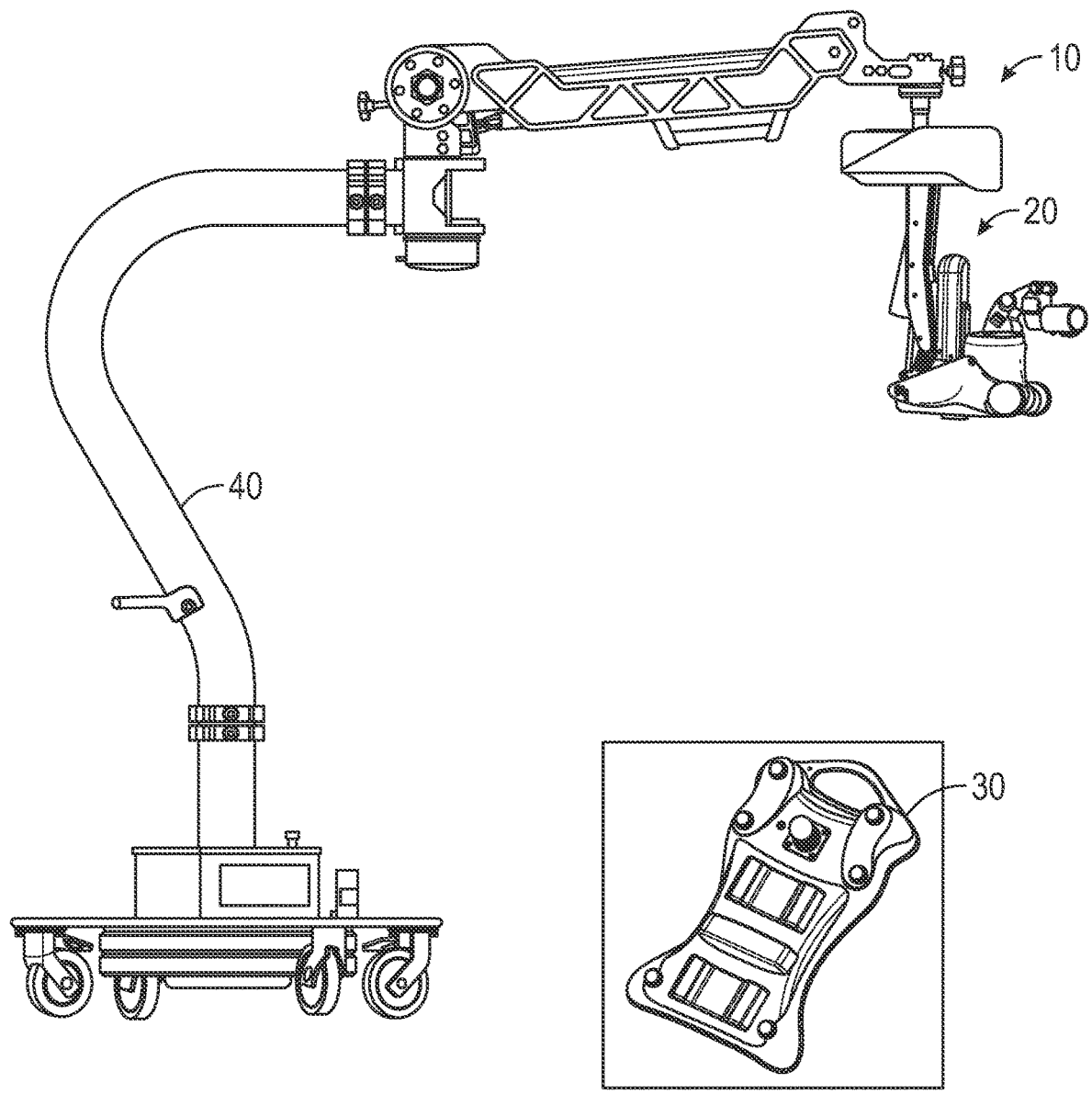
FIG. 1 schematically illustrates an example of a surgical microscope system showing a head unit assembly configured to connect to a floor stand that can be used in the exemplary surgical microscope system.

The present invention can be understood more readily by reference to the following detailed description, examples, drawings, and claims, and their previous and following description. However, before the present devices, systems, and/or methods are disclosed and described, it is to be understood that this invention is not limited to the specific devices, systems, and/or methods disclosed unless otherwise specified, and, as such, can, of course, vary. It is also to be understood that the terminology used herein is for the purpose of describing particular aspects only and is not intended to be limiting.

The following description of the invention is provided as an enabling teaching of the invention in its best, currently known embodiment. To this end, those skilled in the relevant art will recognize and appreciate that many changes can be made to the various aspects of the invention described herein, while still obtaining the beneficial results of the present invention. It will also be apparent that some of the desired benefits of the present invention can be obtained by selecting some of the features of the present invention without utilizing other features. Accordingly, those who work in the art will recognize that many modifications and adaptations to the present invention are possible and can even be desirable in certain circumstances and are a part of the present invention. Thus, the following description is provided as illustrative of the principles of the present invention and not in limitation thereof.

As used throughout, the singular forms "a," "an" and "the" include plural referents unless the context clearly dictates otherwise. Thus, for example, reference to "a light source" can include two or more such light sources unless the context indicates otherwise.

Ranges can be expressed herein as from "about" one particular value, and/or to "about" another particular value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

As used herein, the terms "optional" or "optionally" mean that the subsequently described event or circumstance can or cannot occur, and that the description includes instances where said event or circumstance occurs and instances where it does not.

The word "or" as used herein means any one member of a particular list and also includes any combination of members of that list. Further, one should note that conditional language, such as, among others, "can," "could," "might," or "can," unless specifically stated otherwise, or otherwise understood within the context as used, is generally intended to convey that certain aspects include, while other aspects do not include, certain features, elements and/or steps. Thus, such conditional language is not generally intended to imply that features, elements and/or steps are in any way required for one or more particular aspects or that one or more particular aspects necessarily include logic for deciding, with or without user input or prompting, whether these features, elements and/or steps are included or are to be performed in any particular embodiment.

The phraseology and terminology used herein is for the purpose of description and should not be regarded as limiting. As used herein, the term "plurality" refers to two or more items or components. The terms "comprising," "including," "carrying," "having," "containing," and "involving," whether in the written description or the claims and the like, are open-ended terms, i.e., to mean "including but not limited to." Thus, the use of such terms is meant to encompass the items listed thereafter, and equivalents thereof, as well as additional items. Only the transitional phrases "consisting of" and "consisting essentially of," are closed or semi-closed transitional phrases, respectively, with respect to any claims. Use of ordinal terms such as "first," "second," "third," and the like in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish claim elements.

Disclosed are components that can be used to perform the disclosed methods and systems. These and other components are disclosed herein, and it is understood that when combinations, subsets, interactions, groups, etc. of these components are disclosed that while specific reference to each various individual and collective combinations and permutation of these cannot be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems can be understood more readily by reference to the following detailed description of preferred embodiments and the examples included therein and to the Figures and their previous and following description.

Figure 2:
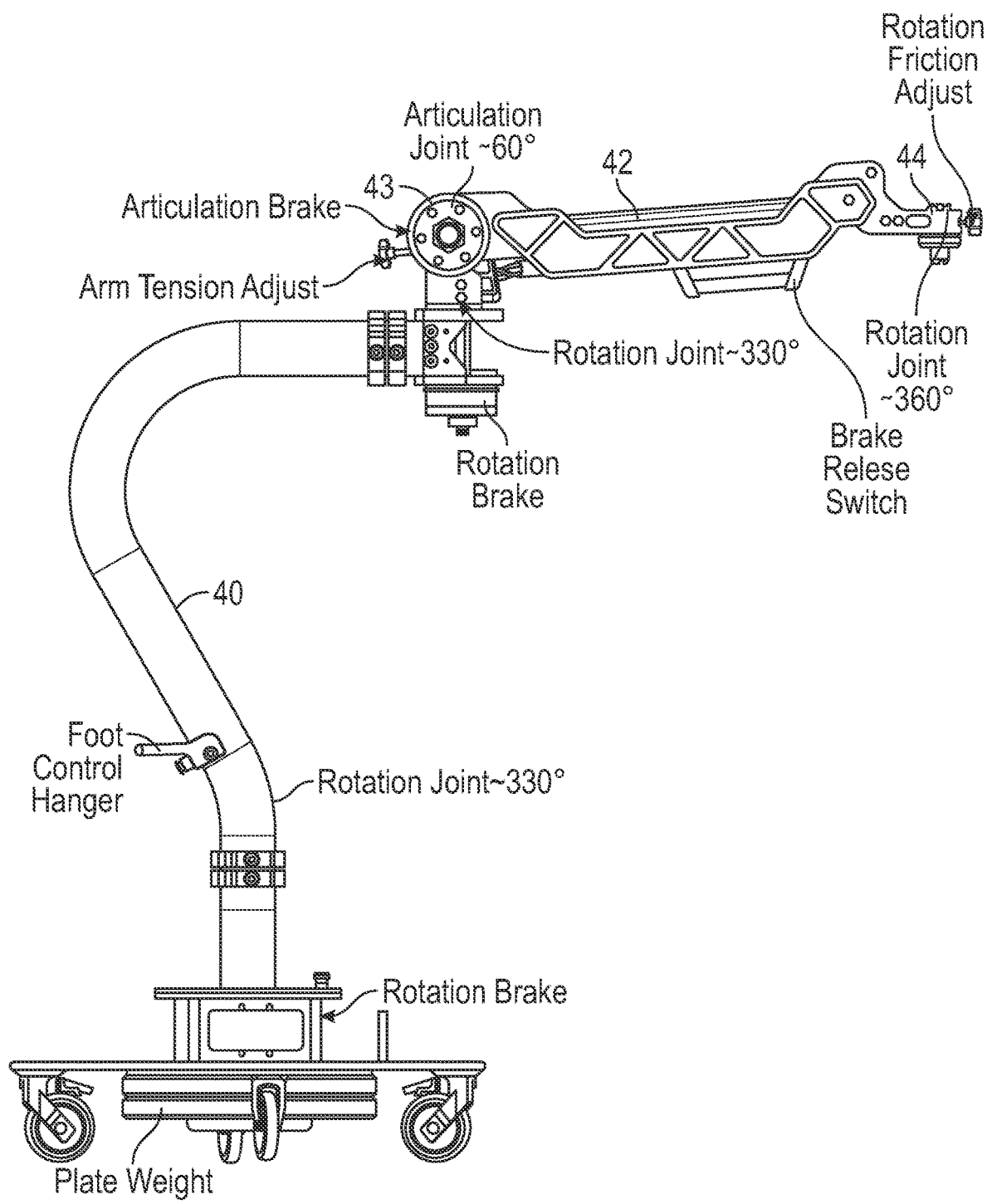
FIG. 2 schematically illustrates the surgical microscope system of FIG. 1.

Turning now to FIGS. 1 and 2, an exemplary surgical microscope system 10 is shown that includes a head unit microscope assembly 20 and a foot control assembly 30 in operative communication with the head unit microscope assembly. As one skilled in the art will appreciate, the foot control assembly 30 can be operatively coupled to the head unit microscope assembly via a conventional cable run or via a wireless connection. As shown, the head unit microscope assembly 20 can be configured to selectively couple to a floor stand assembly 40 such that the that the head unit microscope assembly 20 can be positioned in a desired operative location by the user.

In various aspects, the exemplary surgical microscope system 10 can also include one or more of: a remote viewing assembly 50 in operative communication with the head unit microscope assembly; and/or a head rest assembly 60 that is configured to allow a surgeon to rest their head into a custom fit support device in order to alleviate strain on the surgeon's neck and upper back muscles by allowing the surgeon to rest the weight of his/her head against the face piece during surgery.

Head Unit Microscope Assembly

Figure 3:
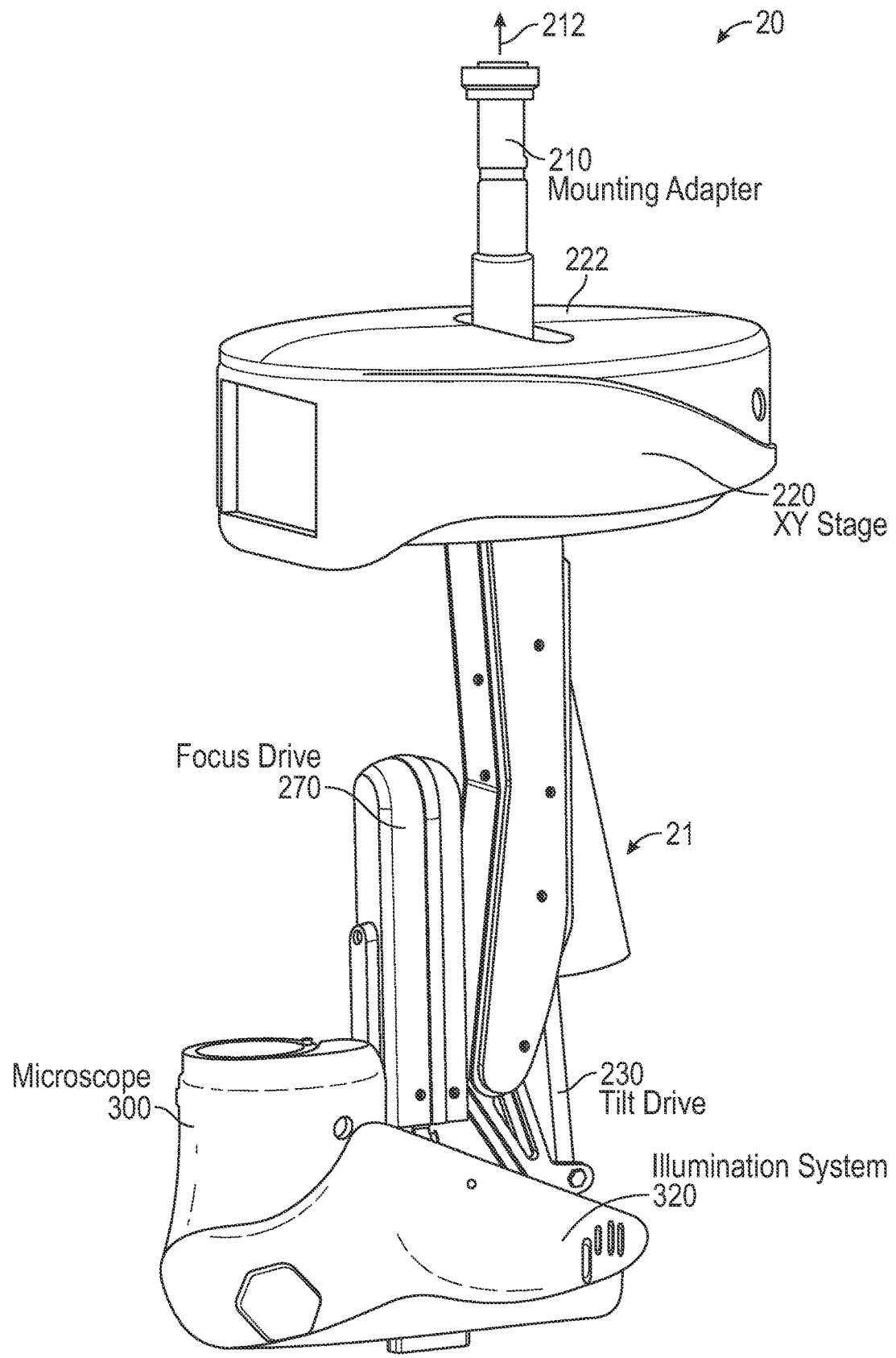
FIG. 3 schematically illustrates an example of a head unit assembly for the surgical microscope system, showing a mounting adaptor, an XY directional stage, a tilt drive, a focus drive; a microscope subassembly, and an illumination system.

In one aspect, and as schematically shown in FIG. 3, the head unit microscope assembly 20 for the surgical microscope system can include one or more of: a mounting adaptor 210, an XY directional stage 220, a tilt drive 230, a focus drive 270; a microscope subassembly 300, and/or an illumination system 320.

In this aspect, it is contemplated that the mounting adaptor 210 of the head unit microscope assembly 20 can be configured to operatively couple to any existing surgical microscope floor stand, regardless of brand, which allows for upgrade of a surgical microscope's optical portion to provide functions and benefits that are not currently available in dated prior existing surgical microscopes. In one aspect, the mounting adapter 210 can comprise an elongated member that extends outwardly from the top surface 222 of the XY directional stage 220 along a mount axis 212. In this aspect, the mounting adaptor can be configured to be received within a complementary bore defined in a distal mount portion 42 of the floor stand 40. In a further optional aspect, the top surface of the XY directional stage 220 can define a mount port that is configured to accept mounting adaptors that are compatible with a conventional floor stand that the user would like to use with the head unit microscope assembly 20. In this aspect, the mount port can have a dovetail form for selective receipt of the selected mounting adaptor. Optionally, the mounting adaptor 210 can be coupled to a complementary mounting post 213 extending outwardly from the XY directional stage 220. In one example, one skilled in the art will appreciate that the top surface 222 can define a plurality of bores that define a plurality of bolt patterns that are configured to allow for the complementary receipt of plates, posts or other adaptors such that the head unit microscope assembly 20 can be operatively coupled to any existing surgical microscope floor stand.

When coupled to the floor stand, the mount axis 212 of the mount adaptor is positioned in a Z axis and the XY directional stage 220 is configured to allow for the selective movements of a distal yoke portion 21 of the head unit microscope assembly 20 in a plane defined by the X and Y axis. Thus, during surgery, if the surgeon wants to see different anatomy or the patient has moved, user-controlled movement of the distal yoke portion of the head unit microscope assembly 20 along the defined XY plane allows for changing the relative positioning of the microscope.

Figure 4:
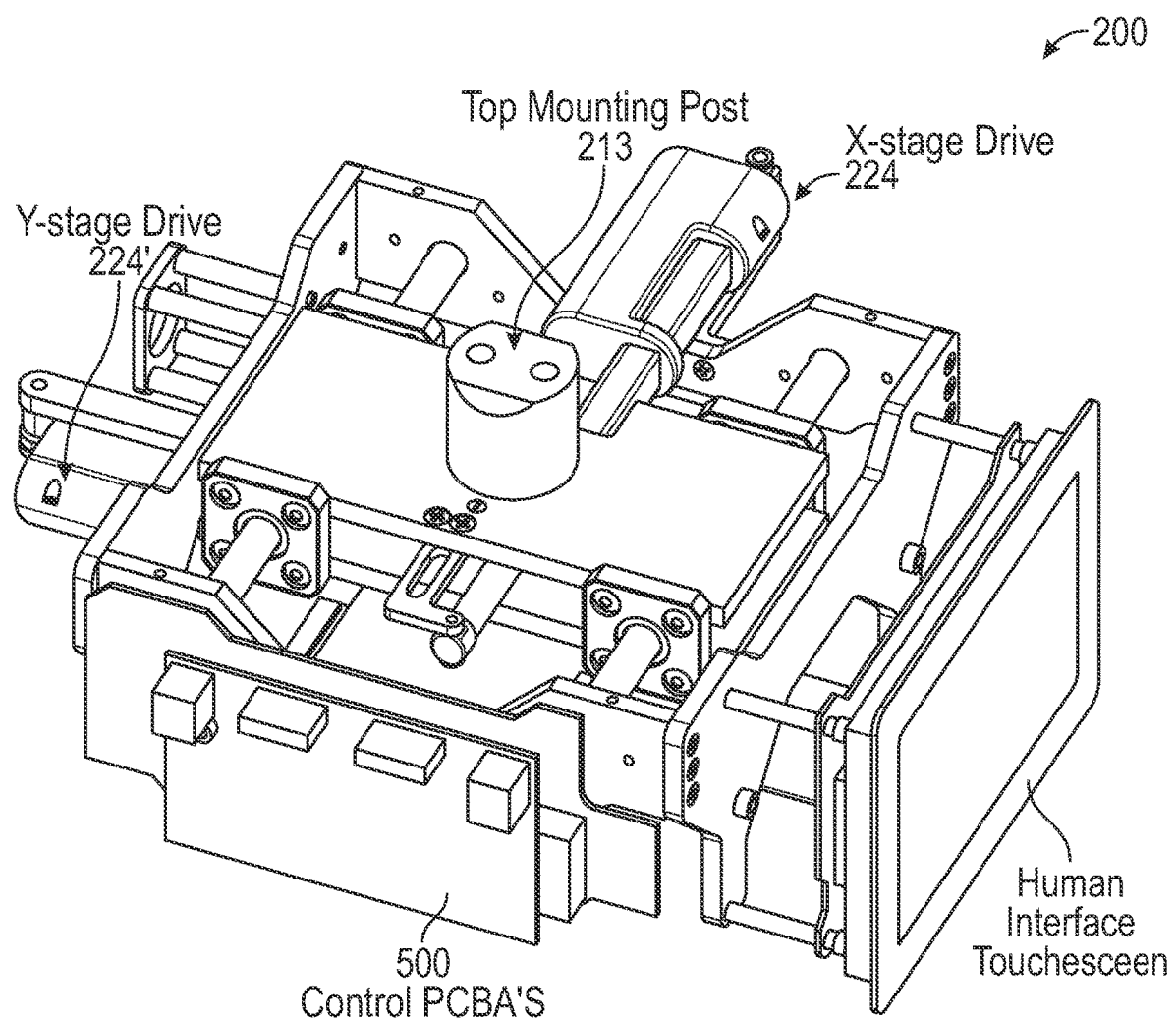
FIG. 4 schematically illustrates an example of an XY directional stage that is configured to for controlling the movement of the head unit assembly with respect to the floor stand along an X-Y plane, right-left and forward-back.
Figure 5:
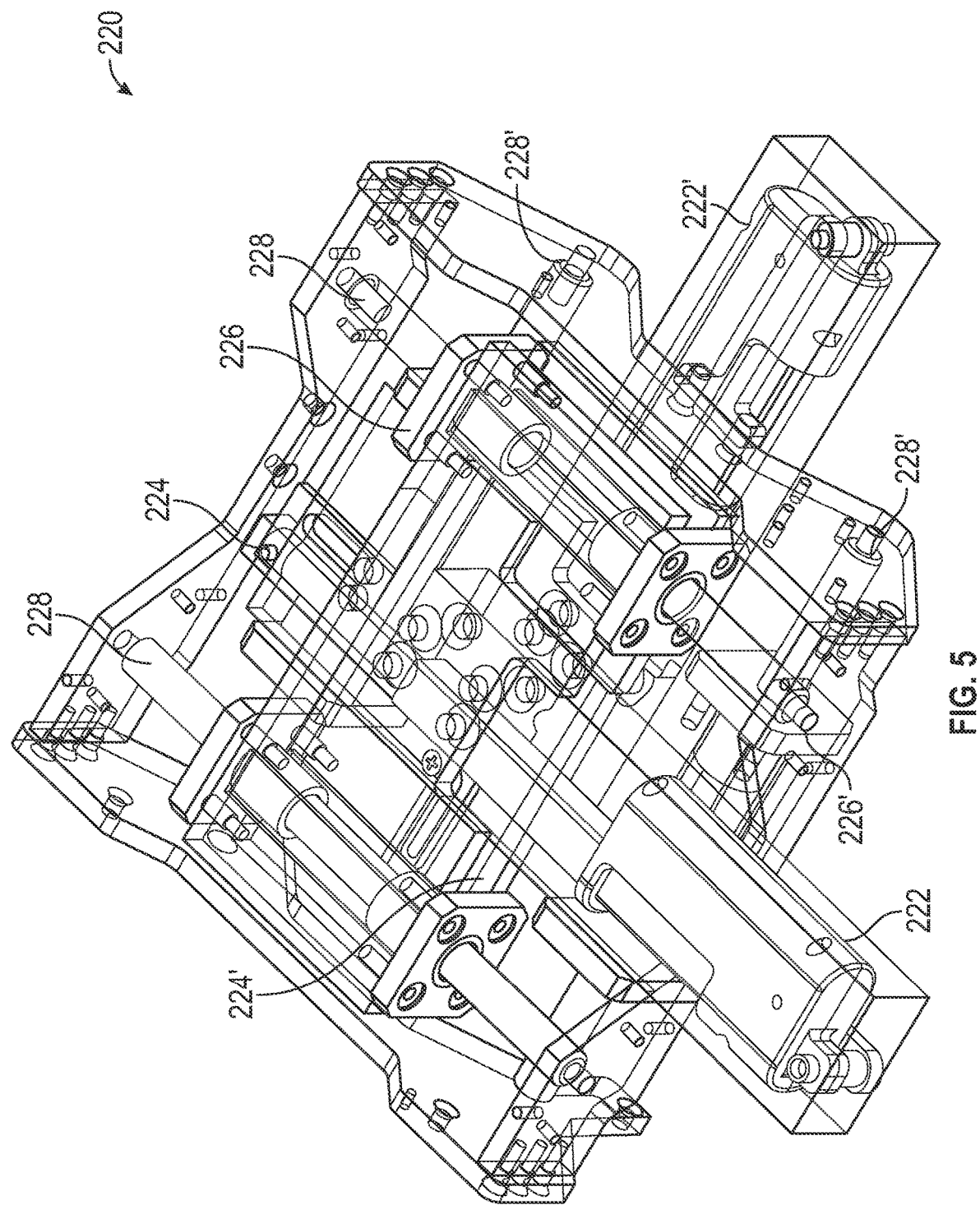
FIG. 5 schematically illustrates a partially transparent example of an XY directional stage that is configured to for controlling the movement of the microscope subassembly with respect to the mounting adaptor along an X-Y plane, right-left and forward-back.
Figure 6:
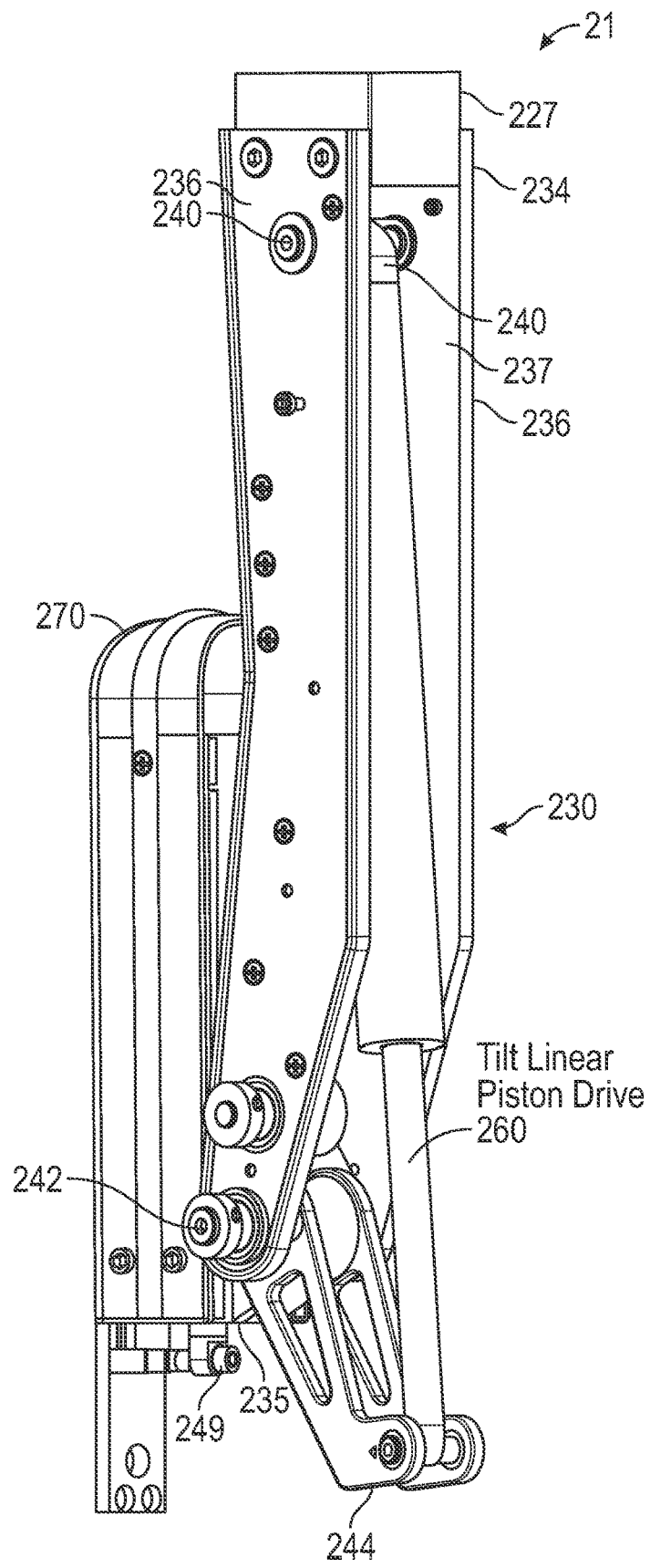
FIG. 6 schematically illustrates an example of a tilt drive that is configured for controlling the angular movement of the microscope subassembly with respect to the longitudinal axis of the mounting adaptor.
Figure 7:
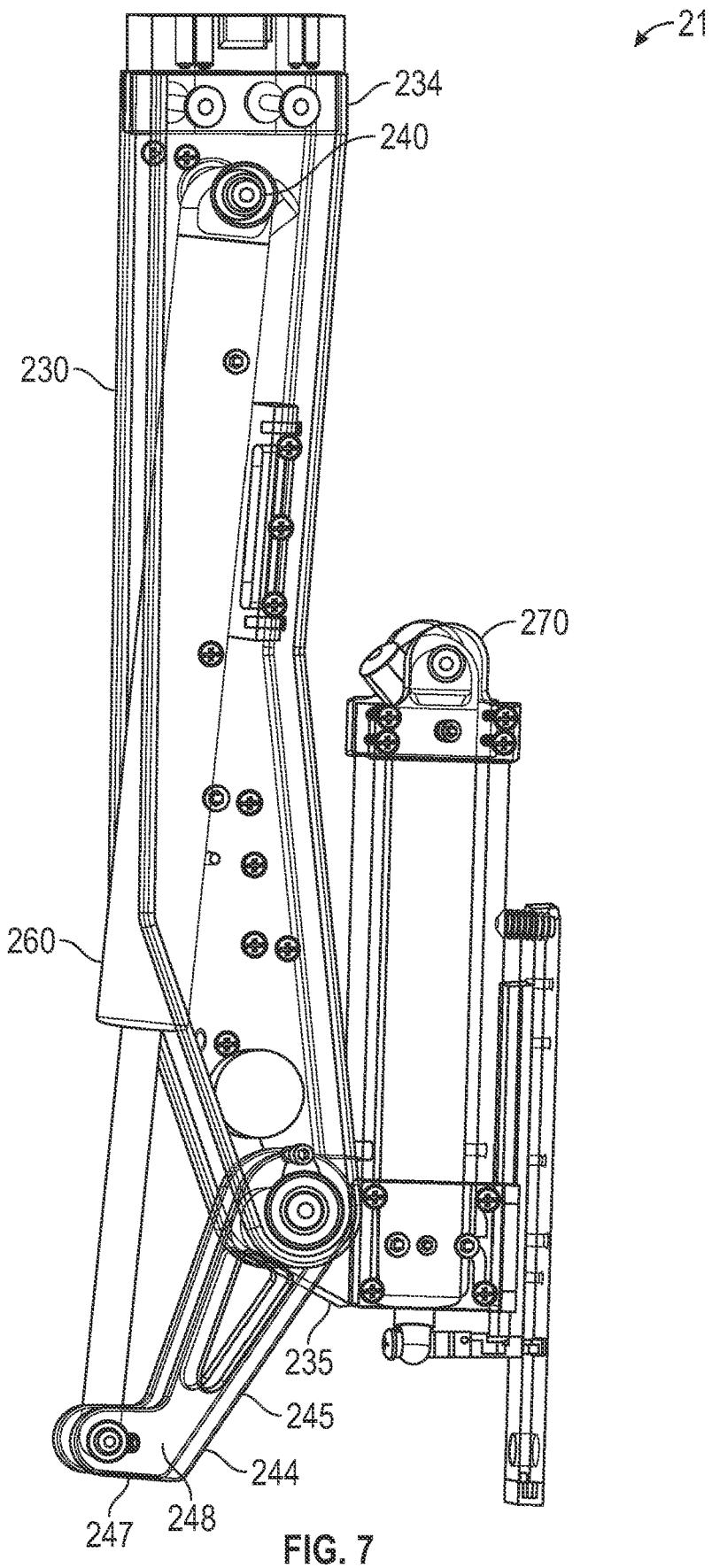
FIG. 7 schematically illustrates a partially transparent example of the tilt drive of FIG. 6.
Figure 8:
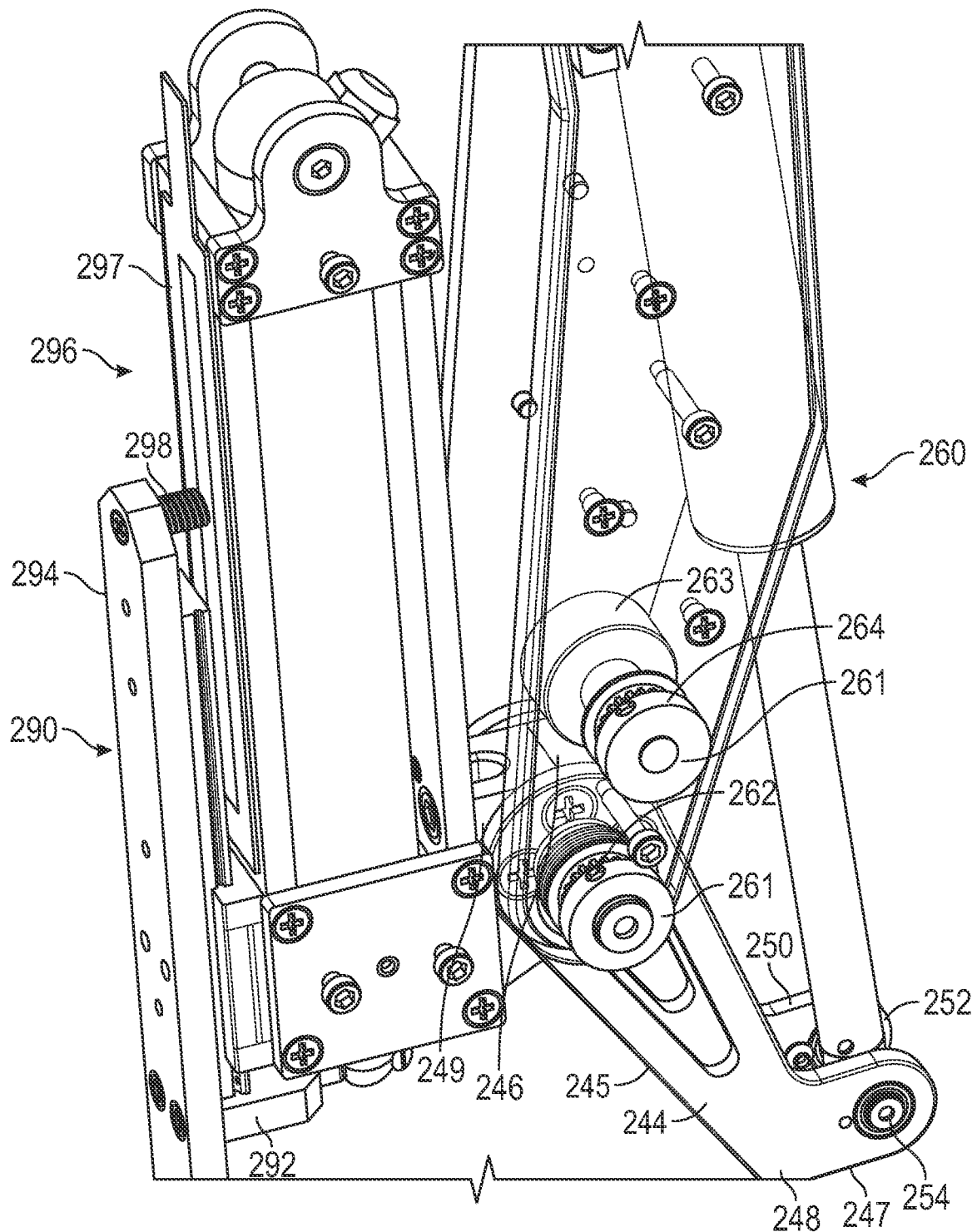
FIG. 8 schematically illustrates an enlarged view of the tilt drive of FIG. 5, showing a first and second gear.
Figure 9:
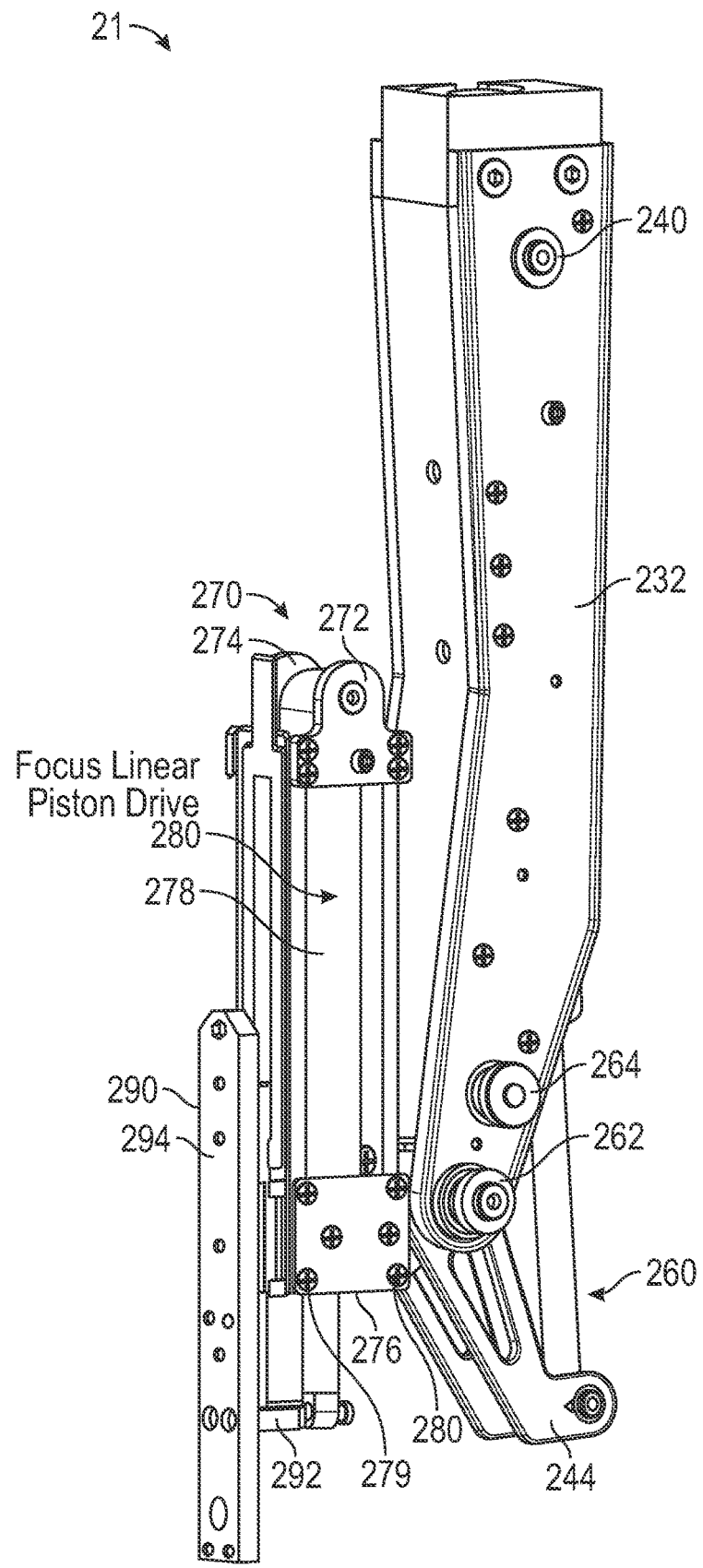
FIG. 9 schematically illustrates an example of a focus drive that is configured to for controlling the movement of the microscope subassembly along a Z-axis relative to the selective operative axis of the tilt drive.

Referring to FIGS. 4 and 5, an exemplary XY directional stage 220 is shown. As exemplary illustrated, the XY directional stage 220 includes two linear piston drives 222, the respective piston drives 222 being positioned at right angles relative to each other in along respective X and Y axis. Each piston drive 222, 222' has an actuator 224, 224' that is coupled to a cradle 226, 226' that is configured for slideable bi-axial movement along a respective X or Y axis. Further, each cradle 226 is slideably mounted to an opposed pair of rods 228, 228' that extend between opposing wall frames 229, 229'. As one will appreciate, the respective axis of the pair of rods 228, 228' are parallel and co-axial to the axis of movement of the respective actuator 224, 224'.

In another optional aspect, it is contemplated XY directional stage 220 can further include a pair of linear potentiometers. In this aspect, each linear potentiometer would be configured to monitor the position of the XY directional stage 220 along a respective X or Y axis.

As exemplarily shown, the XY directional stage 220 is configured to operate the electrically controlled and driven movement of the head unit microscope assembly 20 on an substantially horizontal X and Y plane. Exemplary linear piston drives 222 include, without limitation, linear drives manufactured by are Actuonix, Firgelli, and the like. These exemplary linear piston drives 222 are capable of providing linear movement with positional resistive feedback. Thus, the linear piston drives 222 are configured to provide a signal that is indicative of "where" the respective linear drive is located within the linear piston drive's positional range of movement and also provide a signal indicative of whether the respective linear piston drive has reached, or optionally, is approaching a respective limit end excursion of the respective positional range of movement. As one will appreciate, such positional feedback can also allow for the system to be selectively configured to "recenter" the respective linear piston drives 222 along one or more of the respective X and Y axis's positional range of movement to a selected or "central" position. One will appreciate, the "central" position can be any position that is selected by the operator for this "recenter" operation.

It will be appreciated that the XY directional stage 220 is electrically controlled and the exemplary linear piston drives 222 are capable of operating singly, to provide single directional movement along a respective X or Y axis or in simultaneous mode to provide diagonal movement along the XY plane. As described below, the movements of the XY directional stage 220 can be controlled by a foot control and/or by on-screen controls as needed by the user.

The distal yoke portion 21 of the head unit microscope assembly 20 includes the tilt drive 230 and the focus drive 270. Referring to FIGS. 6-9, the tilt drive 230 is configured to provide electrically controlled and driven angular tilt of the microscope. As shown, the tilt drive allows for relative tilt movement head unit microscope assembly 20 and that this relative tilt movement is configured to occur between the focus drive 270 and the XY directional stage 220. One skilled will appreciate that the drive axis of the focus drive 270 is technically a Z-axis with respect to the optical viewing axis. As shown, movement along the drive axis of the focus drive 270 is allows for the selective movement of the microscope closer to or further away from the patient. Thus, if the microscope is tilted to some degree, the "focus" movement along the drive axis of the focus drive 270 needs to move along that same "angle," e.g., along a common axis, to provide true focus.

As shown, the tilt drive 230 can comprise a housing 232 having a distal end 234 and a proximal end 235. The housing 232 has a pair of opposed parallel side walls 236 that define an interior cavity 237. The proximal end of the housing is fixedly mounted to a post 227 extending distally from the XY directional stage 220. Adjacent the proximal end 235 of the housing, a first axle 240 is mounted to the respective side walls 236, which first axle extends transverse to the opposed parallel side walls. Similarly, adjacent the distal end 234 of the housing, a second axle 242 is mounted to the respective side walls 236, which second axle extends transverse to the opposed parallel side walls.

As shown, the tilt drive 230 further comprises a linear piston drive 260 and a drive member 244. Exemplary linear piston drive 260 includes, without limitation, linear piston drives manufactured by are Actuonix, Firgelli, and the like. These exemplary linear piston drives 260 are capable of providing linear movement with positional resistive feedback. In this aspect, the drive member 244 comprises a first member 245 having a proximal end 246 that defines a bore that is sized and shaped to complementary receive the second axle 242 of the housing. Thus, in operation, the drive member 244 can be selectively rotated about the second axle 242. The drive member 244 further includes a second member 247 that is integrally connected to the distal end 248 of the first member 245 and that extends outwardly relative to the drive member at an obtuse angle. The second member 247 has a pair of opposed parallel second member side walls 250 that define an interior cavity 252. As shown, proximate the distal end 252 of the second member 247, a third axle 254 is mounted to the respective second member side walls 250, which third axle 254 extends transverse to the opposed parallel side walls. The linear piston drive of the tilt drive is coupled to the respective first and third axles and extends at least partially within the interior cavity 237 of the housing 232. In operation, the selective activation of the linear piston drive 260 allows for the selective rotation of the drive member 244 about the axis defined by the second axle 242.

In another optional aspect, it is contemplated that the tilt drive 230 can be configured to generate a signal that is indicative of the position of the linear piston drive 260 and/or the amount of "tilt," e.g., the rotational position of the drive member relative to an elongate axis of the housing of the tilt drive 230. In operation, it is optionally contemplated that the system can provide at least one, or a plurality of, pre-determined tilt positions that can be selected by the operator for respective operative procedures. In various non-limiting exemplary aspects, it is contemplated that such a signal can be generated by a rotary potentiometer or via the use of a conventional MEMS inclinometer.

In one optional aspect, it is contemplated the tilt drive 230 can further include at least one rotary positional sensor 261. In this aspect, a first gear 262 can be operatively coupled to the proximal end of the first member of the drive member such that it is configured to rotate about an axis co-axial to the axis of the second axle of the tilt drive. A second gear 264 can be mounted on to a fourth axle mounted within the interior cavity of the wall members. A continuous belt, not shown, operably connects the first and second gears. Further, in this aspect, it is contemplated that rotational potentiometers 263 coupled to the respective first and second gears can be configured to monitor the rotational position of the drive member relative to an elongate axis of the housing of the tilt drive 230. In operation, as the tilt drive 230 is actuated, the coupled shafts are rotated, relative to the amount of tilt, which is then seen by the potentiometer as a variable resistive load. In this aspect, a conventional ADC circuit reads the value and generative a signal indicative of the relative amount of tilt.

In a further optional aspect, a MEMS inclinometer can be coupled to the tilt drive 230. In one example, the MEMS inclinometer can be an IMU (Inertial Movement Unit) manufactured by Murata Electronics, which is a solid-state device IC with digital communication capabilities. The MEMS inclinometer is configured to generate a signal indicative of the relative amount of tilt of the tilt drive that is relative to Earth's gravity.

The drive member 244 further defines a mounting surface 249 positioned on a portion of the proximal end of the first member 247. As shown in the figures, the focus drive 270 is mounted to the mounting surface 249. The focus drive 270 has a housing 272 having a proximal end 274 and a distal end 276 and parallel opposing walls that define an interior cavity 278. In the exemplary figures, a distal portion 280 of the housing 272 is mounted to the mounting surface 249 of the drive member 244. As one will appreciate, as the drive member 244 is operatively rotated relative to the elongate axis of the housing of the tilt drive 230, the housing 272 would be complementarily rotated in a plane that bisects the elongate axis of the housing 232 of the tilt drive 230.

The focus drive 270 includes a linear actuator drive 280 that is mounted within the interior cavity 278 of the housing and extends along a drive axis that is co-axial to the elongate axis of the housing. Exemplary linear actuator drives 280 include, without limitation, linear actuator drives manufactured by are Actuonix, Firgelli, and the like. These exemplary linear actuator drives 280 are capable of providing linear movement with positional resistive feedback. As previously described, the focus drive allows for the electrically controlled and driven bi-axial movement of the microscope along an axis that is defined by the position of the tilt drive 230. On skilled in the art will appreciate that the axis for focus is with respect to the optical axis and is not necessarily co-incident with the mount axis. It will be appreciated that the focus drive 270 can be controlled by a foot control and/or by on-screen controls as needed by the user.

The linear actuator drive 280 is configured to provide a signal that is indicative of "where" the linear actuator drive 280 is located within the linear piston drive's positional range of movement and also provide a signal indicative of whether the linear actuator drive 280 has reached, or optionally, is approaching a respective limit end excursion of the positional range of movement. As one will appreciate, such positional feedback can also allow for the system to be selectively configured to "recenter" the linear actuator drive 280 along the drive axis's positional range of movement to a selected or "central" position. One will appreciate, the "central" position can be any position that is selected by the operator for this "recenter" operation.

The proximal end of the linear actuator drive is mounted within the interior cavity of the housing at the proximal end of the housing. In operation, portions of the actuator of the linear actuator drive are configured to extend through an opening 279 defined in a distal end of the housing. As one will appreciate, the actuator is configured for bi-axial movement along a defined drive axis that is co-axial to the elongate axis of the housing of the focus drive 270.

The focus drive 270 further includes a mount member 290 that has a first mount 292 that is connected to, and extends transversely too, the distal end of the actuator of the linear actuator drive. The mount member further includes a second elongate mount 294 that is connected to a distal edge of the first mount such that the second elongate mount is positioned transverse to the first mount and has a longitudinal axis that is parallel to the elongate axis of the housing of the focus drive 270. As one will appreciate, selective actuation of the focus drive allows for the movement of the second elongate mount relative to the distal end of the housing of the focus drive 270 and along a plane that bisects the drive axis of the actuator.

In another optional aspect, it is contemplated the focus drive 270 can further include a positional sensor 296, such as, for example and without limitation, a linear potentiometer. In this exemplary aspect, an elongate touch pad 297 can be mounted onto an exterior surface of a wall of the housing of the focus drive 270 that is positioned in spaced opposition to an inwardly facing exterior surface of the second elongate mount. Further, a pin 298, which extends outwardly from the inwardly facing exterior surface of the second elongate mount, can be configured to selectively contact the touch pad such that the pressure contact of the pin against the touch pad can be sensed. Thus, the relative linear distance that the second elongate mount moves relative to the distal end of the housing of the focus drive 270 can be sensed and a signal can be generated that is indicative of the position of the second elongate mount relative to the distal end of the housing of the focus drive 270.

Figure 10:
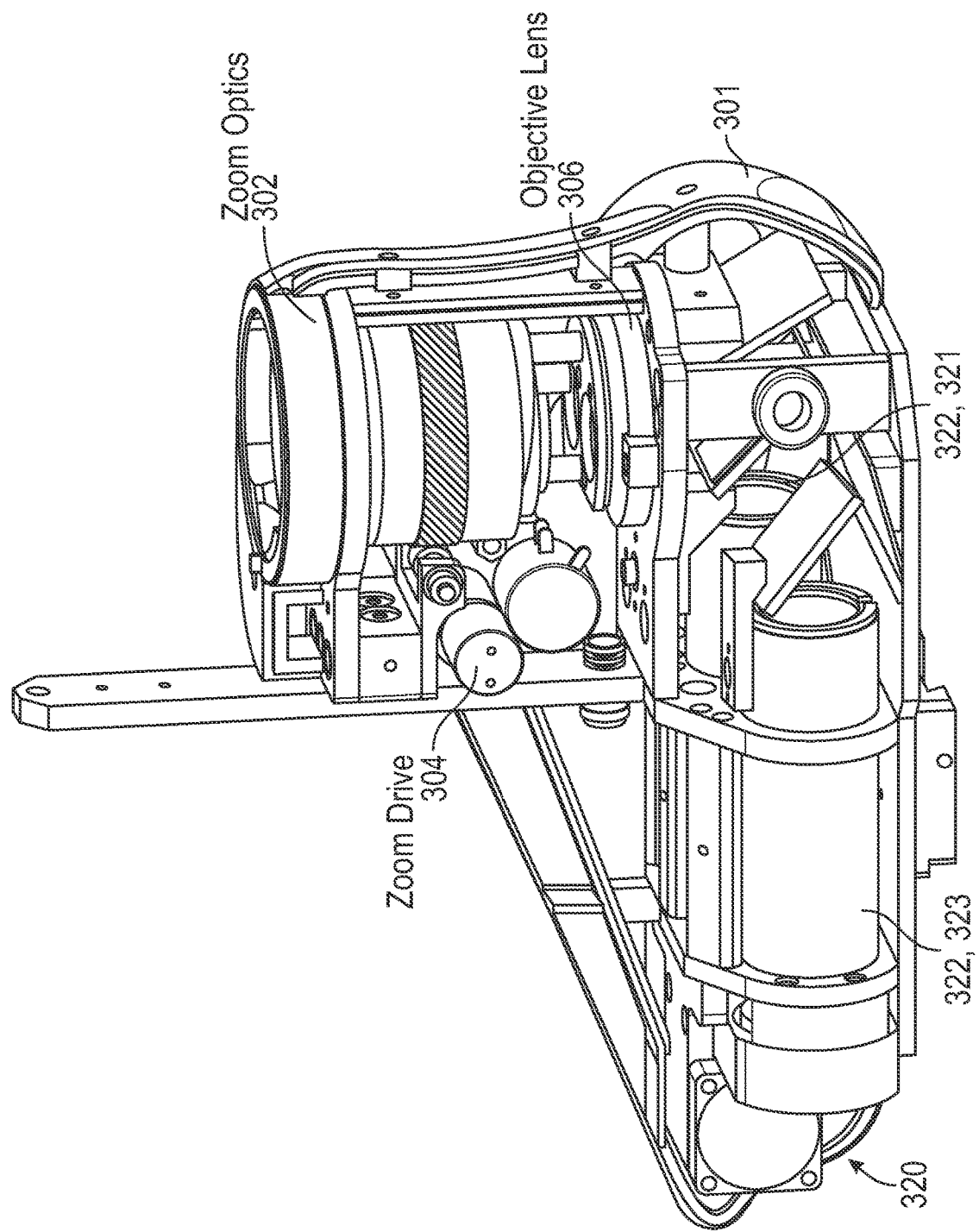
FIG. 10 schematically illustrates an example of a microscope subassembly that is configured to mount to the focus drive of FIG. 9.

Referring now to FIGS. 3 and 10, the microscope subassembly 300 is connected to the outwardly facing exterior surface of the second elongate mount. The microscope subassembly 300 further has a housing 301 into which a zoom optics module 302, a zoom drive 304, and an objective lens 306 are mounted. As shown in the figures, the zoom optics module 302 is positioned proximal to the zoom drive 304 and the distal most objective lens 306. The respective zoom optics module 302, zoom drive 304, and objective lens 306 are conventional. Further, it is contemplated that the microscope subassembly 300 can further include a binocular optics module 308 that is conventional and is configured to conventionally mount thereto the proximal end of the zoom optics module.

Figure 11:
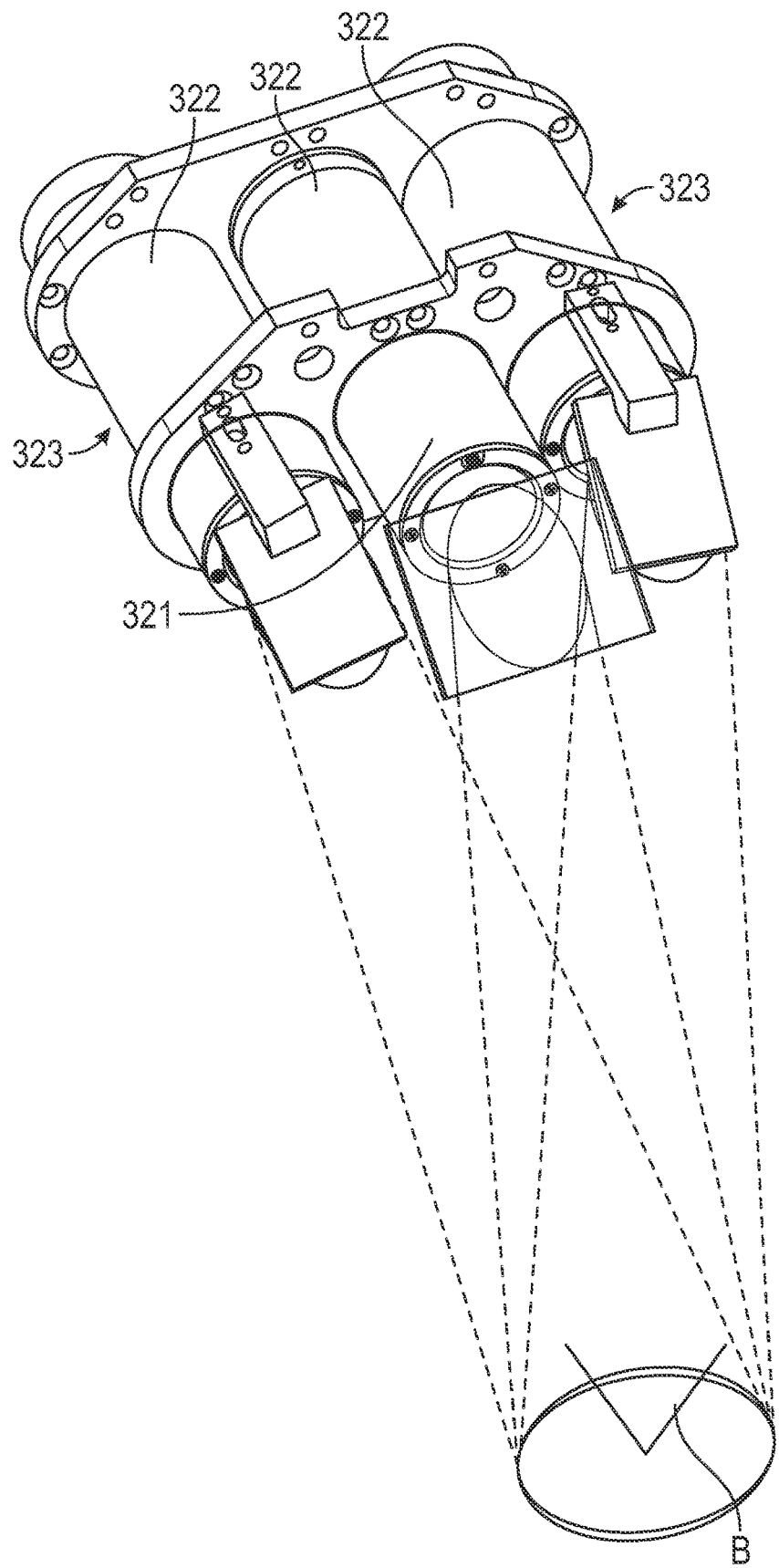
FIG. 11 schematically illustrates an example of a microscope subassembly that is configured to use three light sources for illumination—two oblique and one central or coaxial, which light sources can be independently controlled to allow the user to fine tune the ratio of light directed to the target tissue.

Referring to FIG. 11, the microscope subassembly 300 further includes the illumination system 320, which comprises three light sources 322 for illumination of the targeted tissue area. As shown, one of the light sources 322 is a central or coaxial light source 321 and the remaining pair of light sources are off-axis or oblique lights sources 323. It is contemplated that the intensity of at least one of the light sources can be controlled to fine tune the ratio of light between the coaxial light source and the pair of oblique light sources. Optionally, it is contemplated that the intensity of each of the light sources can be controlled to fine tune the ratio of light between the coaxial light source and the pair of oblique light sources. In a further optional aspect, it is contemplated that the color temperature and/or color rendering index (CRI) of one or more of the respective light sources 322 can be selectively controlled.

In this aspect, the user control of the ratio of light from the respective coaxial and oblique light source is beneficial in surgical contexts. For example, in eye surgery, coaxial light illumination provides desired levels of red reflex for cataract surgery and illumination penetration, while oblique light illumination can provide desired levels of depth perception and edge detection. For example, and without limitation, the user can select the ratio of light between the coaxial light source and the pair of oblique light sources to be approximately 80% of the light impacting the targeted tissue to from the divergent coaxial light beam and the remaining 20% from the pair of divergent oblique light beams.

In operation, it is further contemplated that when a user initiates the illumination system 320 of the microscope subassembly 300, the user can manually adjust the ratio of light between the coaxial light source 321 and the pair of oblique light sources 323 to obtain a user preference light ratio level setting. In an optional aspect, it is further contemplated that the user can select to save the user preference light ratio level setting in the control subsystem 500 such that when the user resets the illumination system 320, the user preference level setting is recalled. As one will also appreciate, it is contemplated that when a user has set or selected a desired ratio of light between the coaxial light source 321 and the pair of oblique light sources 323, the user can subsequently selectively change, i.e., increase and/or decrease, the overall light intensity supplied the illumination system 320 while maintaining the selected light ratio level setting.

In one aspect, it contemplated that the respective light sources 322 can have a high CRI level. In this aspect, for various embodiments, the CRI level of the respective light sources 322 can be at least 70, preferably at least 80, more preferably at least 90, with a desired CRI of at least 95. In other aspects, for various embodiments, the CRI level of the respective light sources 322 can be between 70 and 99.9, preferably between 80 and 99.9, more preferably between 90 and 99.9, still more preferably between 95 and 99.9, with a desired CRI between 97 and 99. Generating a high CRI level from the respective light sources 322 aids in providing an accurate color representation, which is difficult in LEDs as conventional LEDs generate peak colors in the blue, green and red spectrums as a result of the conventional use of blue, green and red bulbs is the respective LED.

In ophthalmologic surgery procedures, red reflex, which is incident light that is reflected off of the patient's retina, allows a surgeon to visualize clear and semi-clear tissues in the eye. Since the retina of the patient is full of blood, the light that is most reflected would be in the red spectrum of light. In one aspect, the respective light sources 322 can be selected or otherwise configured to generate a high percentage level of normalized radiant power in the red spectrum; i.e., it is preferred that the spectrum of light generated by the respective light sources 322 be biased toward providing a peak level of the percentage level of normalized radiant power about the red spectrum. In this aspect, it is preferred that the respective light sources 322 generate a peak percentage level of normalized radiant power having radiation with wavelengths between about 600 and 700 nm; and preferably about 650 nm.

In a further optional aspect, because different pigment eyes respond differently, it is contemplated that the illumination system 320 of the microscope subassembly 300 be configurable by the user to adjust the color temperature and/or spectral makeup of the total light generated by the coaxial light source 321 and the pair of oblique light sources 323 to generate a desired spectrum of incident light in order to obtain a level of desired red reflex from the light illumination incident on the patient's eye.

In yet another exemplary aspect, it contemplated that the respective light sources 322 can be selected or can be otherwise configured to generate a color temperature of that is less than about 4500K, preferably less than 4000K, more preferably less than 3800K, with a desired color temperature of about 3500K. In other aspects, for various embodiments, the color temperature of the respective light sources 322 can be between 2500K and 4500K, preferably between 3000K and 4000K, more preferably between 3100K and 3900K, with a desired color temperature of between 3300K and 3600K. Generating a desired color temperature from the respective light sources 322 in the identified ranges aids in providing an accurate color representation while minimizing the intensity of the light sensed by the patient.

Figure 12:
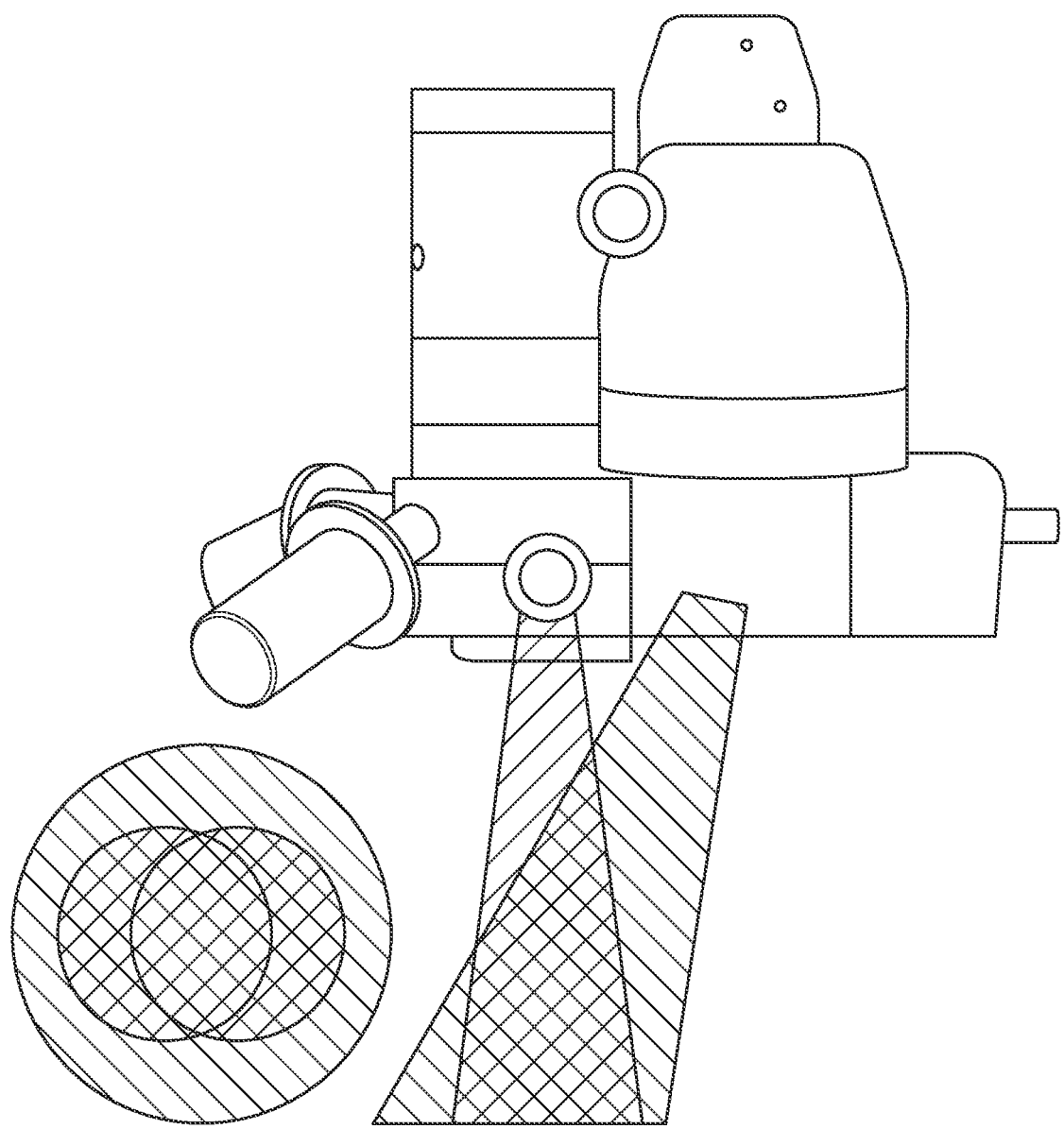
FIG. 12 schematically shows a prior art illumination system that uses two beams of coaxial illumination and one beam of oblique illumination.
Figure 13:
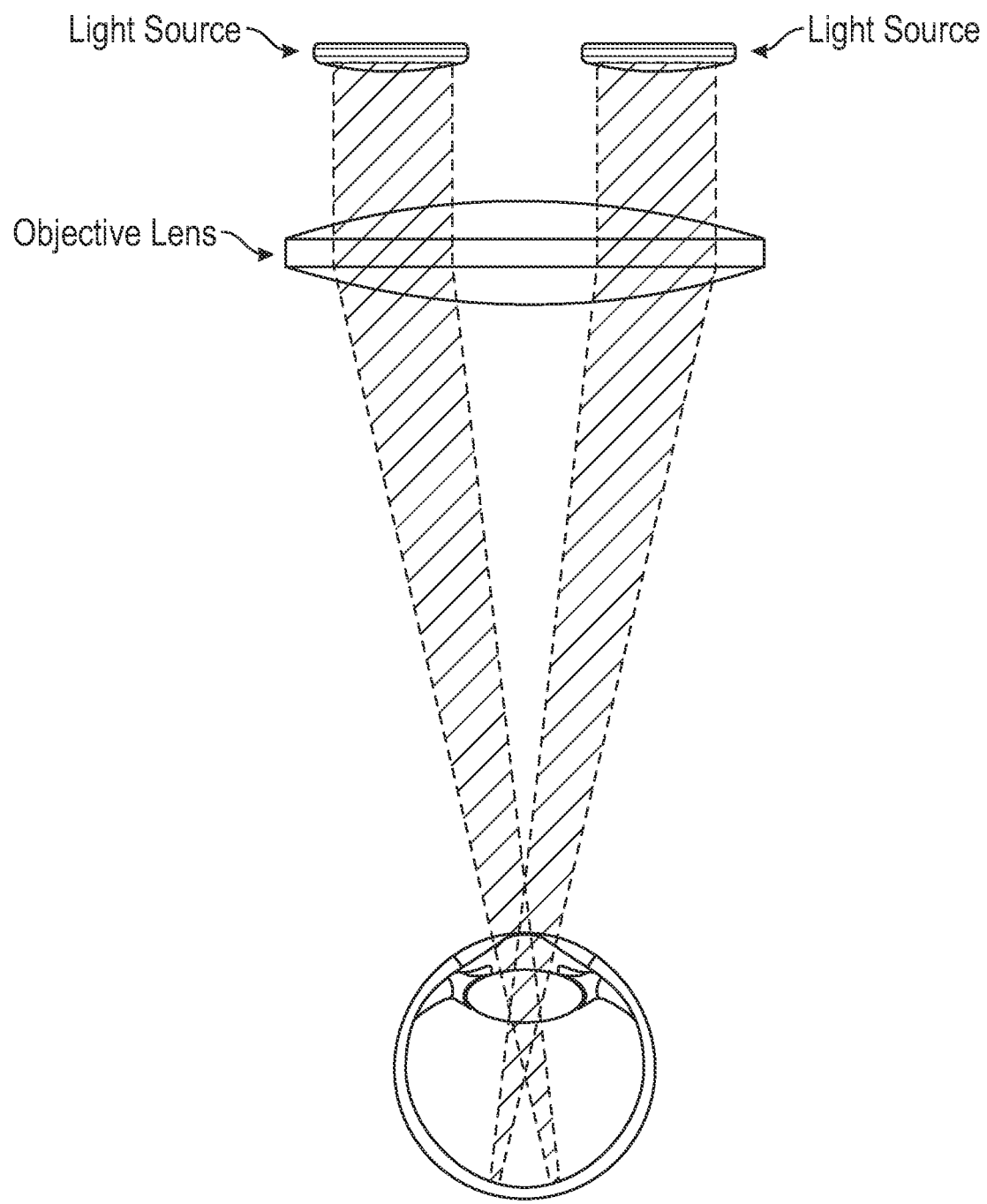
FIG. 13 schematically shows a prior art illumination system in which light energy passes through the objective lens that resultantly provides some general "focused light" or convergence.
Figure 14:
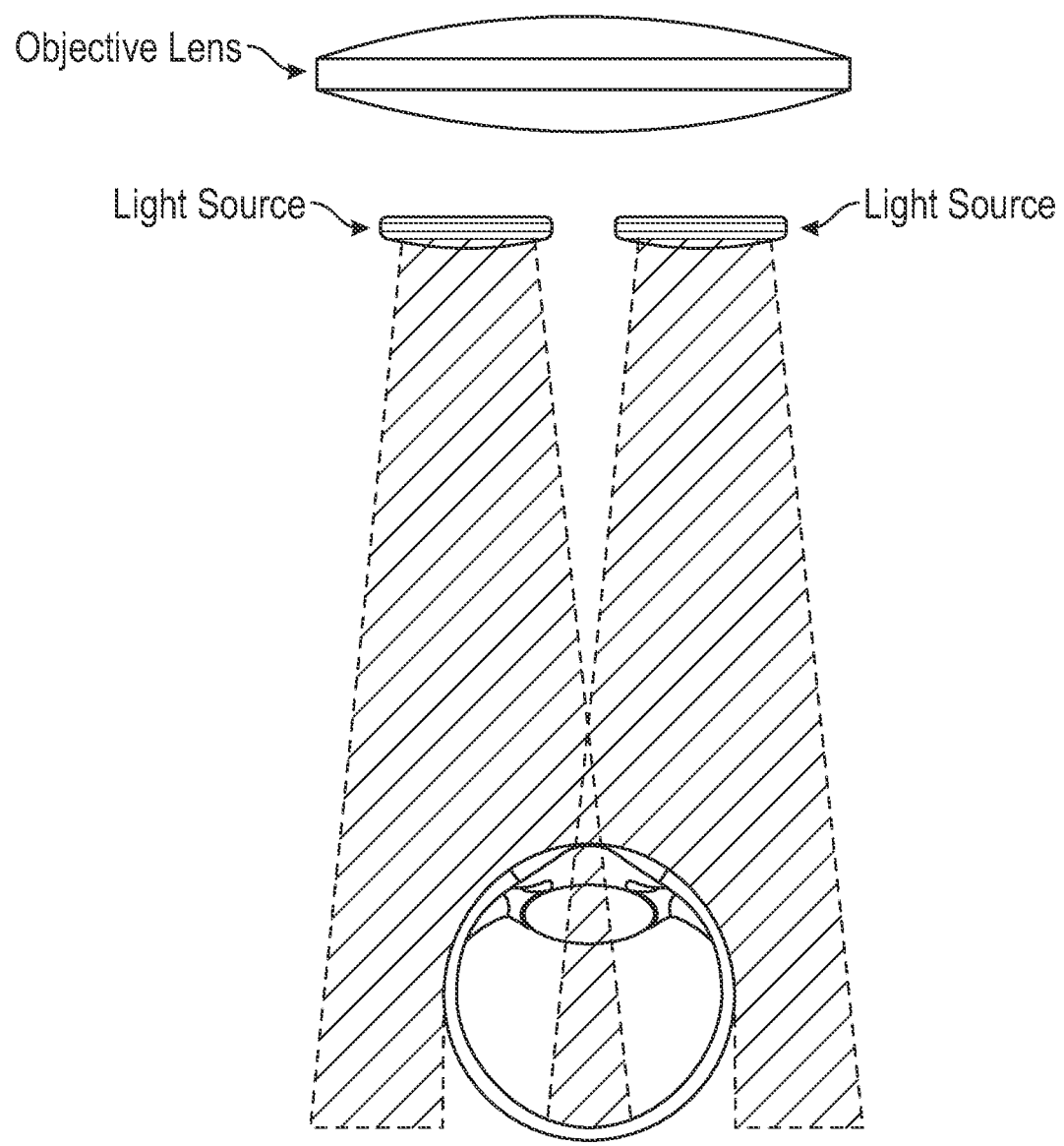
FIG. 14 schematically shows a prior art illumination system in which collimated light, one for each optical pathway—the left and the right eye, is used that does not pass through the objective lens and does not tend to converge.

Referring to FIG. 12, prior art illumination systems typically use two beams of coaxial illumination and one beam of oblique illumination. As illustrated in FIGS. 13 and 14, prior art illumination systems use a beam of coaxial illumination for each of the respective left and right eye optical axis. An accurate representation of the illumination from the prior art illumination systems is shown in FIG. 12, which illustrates overlapping coaxial illumination relative to the oblique illumination. For eye surgery, in the illumination environment provided by these prior art illumination systems, only the area in which the two coaxial lights overlap is appropriate red reflex directed to both of the surgeon's eyes. Thus, in this context and for these prior art illumination systems, if the patient's iris is outside of this overlapping area, the surgeon either receives appropriate red reflex along only one optical pathway, or no red reflex at all.

In other prior art illumination systems and as shown in FIG. 13, the light energy passes through the objective lens that resultantly provides some general "focused light" or convergence. Optionally, as shown in FIG. 14, the prior art illumination system uses collimated light, one for each optical pathway—the left and the right eye, that does not pass through the objective lens and does not tend to converge. In this system, a third light beam is directed at the targeted tissue from an oblique angle to provide for oblique illumination is directed in from about an eight-degree oblique angle.

Figure 15B:
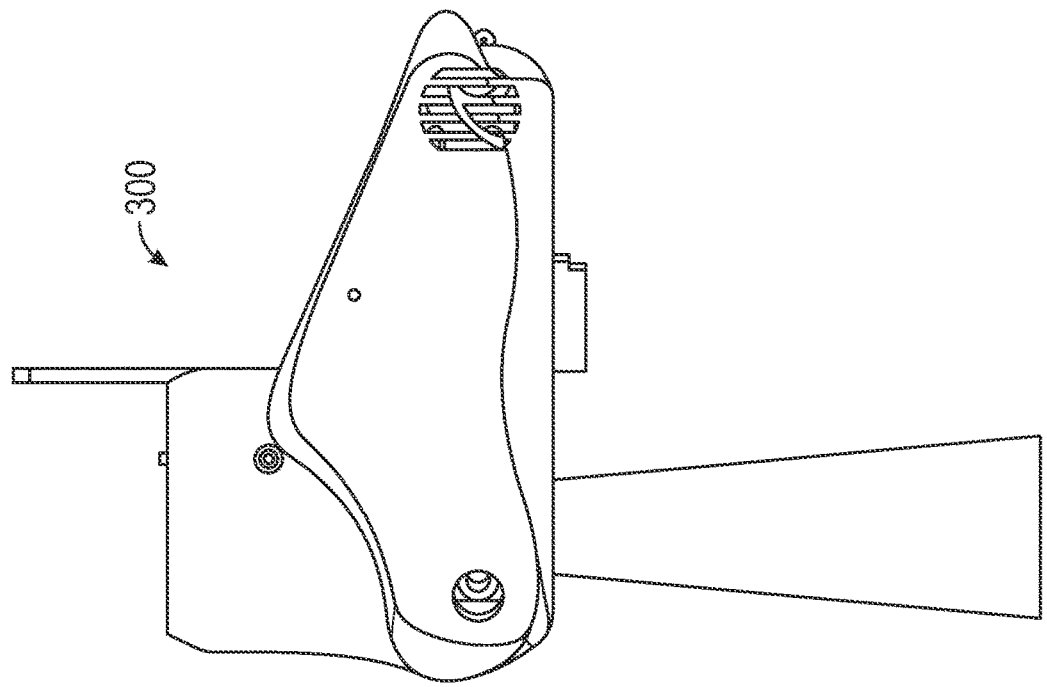
FIGS. 15A and 15B schematically show the application of a single central beam of divergent light to fill the targeted tissue area with light.
Figure 15A:
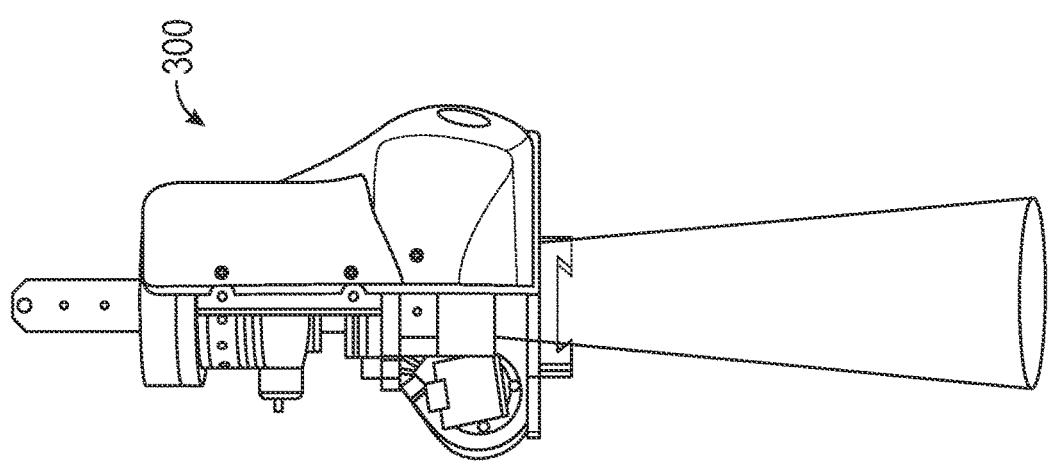
Figure 16:
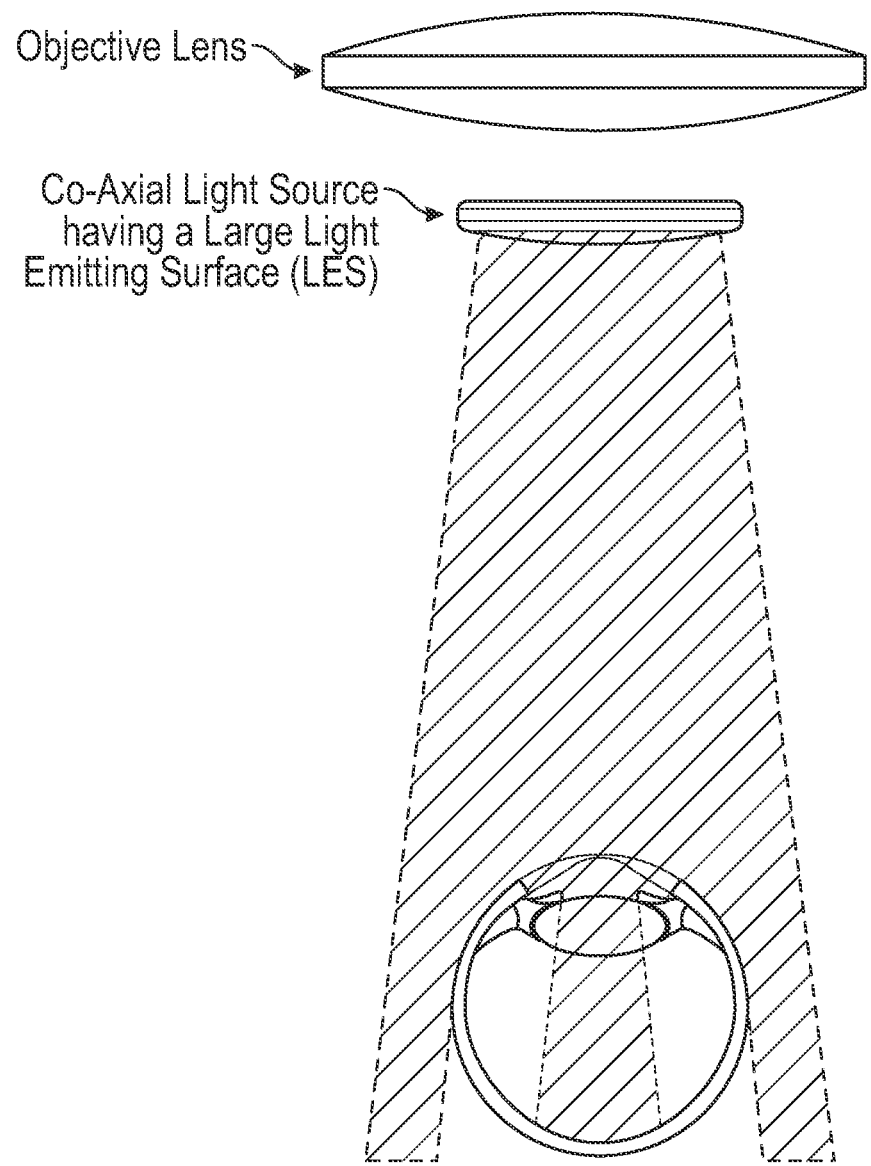
FIG. 16 schematically shows the application of a single central beam of divergent light, which does not pass through the objective lens of the microscope, to fill the targeted tissue area with light.

In one aspect of the illumination system of the present invention, and as shown in FIGS. 15A, 15B and 16, the central or coaxial light source forms a beam of divergent light that does not pass through the objective lens 306 and that is configured or otherwise sized to fill the targeted tissue area with light. In this aspect, the beam of divergent light emits from the center of the surgeon's view, i.e., centered between the surgeon's left and right optical pathways. As shown, the divergent angle of the central or coaxial light source allows for a comparable illumination area that is relative to the oblique illumination at the focal plane.

The central or coaxial light source provides a wider dispersion of light energy on the patient's retina with less concentration when compared to the prior art illumination systems. This wider dispersion of light energy on the patient's retina allows for more of the interior region to be illuminated while also provides for evenly dispersed light energy across the targeted tissue, which provides excellent red reflex effect that is less dependent on the angle or axis of the patient eye. The coaxial light source illumination can fill the entire targeted area of the illumination spot size at the focal plane, which allows for the red reflex area generated by the illumination system, in contrast to the prior art illumination systems, to substantially mirror the illuminated tissue at the focal plane. Thus, in eye surgery, no matter where the patient's eye is during surgery, as long as the patient's eye is receiving illumination from the illumination system, the red reflex will be visualized by the surgeon.

Further, it is contemplated that the wider dispersion of light energy on the patient's retina provided by the illumination system 320 aids in minimizing patient photophobia, which can cause patient discomfort, while also minimizing patient phototoxicity, which can result in undesired light-induced retinal tissue damage. Because the exemplified prior art illumination systems generally all use light sources that narrowly disperse light energy impacting on the patient's retina during surgery, the patient's suffer discomfort from the perceived light induced "hot" or "bright" spot during surgery. Adversely, the patient may also suffer tissue damage due the adverse effects of the narrowly dispersed light energy impacting of the targeted eye tissues over the course of the surgery. As suggested, the large point source of the illumination beams generated by the illumination system 320 and the low relative intensity of the divergent oblique beams contributes to enhanced patient comfort and a minimization of potential eye tissue damage.

In a further aspect, the divergent beam of light generated by the central or coaxial light source 323 of the illumination system can be selectively decreased in diameter when desired by the user. In this decrease in diameter does not increase the intensity of the light energy impacting the targeted tissue, but rather, the illumination system further includes a user modulated clip or iris, positioned distally from the central or coaxial light source, to generate the reduced diameter of the divergent light beam. The clip or iris can be controlled manually via a coupled knob or can be motorized via a servo motor or other mechanism suitable for actuating the diaphragm of the clip or iris. In operation, the selective reduction in the diameter of the divergent light beam generated by the central or coaxial light source can aid in reducing excessive glare and light reflecting from the patient's sclera.

As one skilled in the art will appreciate, oblique illumination is the primary creator of contrast, depth perception, and edge detection for a surgical microscope. illumination coming from an oblique angle creates shadows and helps the user perceive where structure and anatomy are with relation to each other. As illustrated, the illumination system uses the pair of light sources to provide the desired off-axis or oblique lights sources. The oblique and divergent light beams 321 that are generated by each of the oblique lights sources and angled at a desired angle of incidence β, relative to the optical axis. In one aspect, the desired angle of incidence β is between about 5 to 15 degrees, about 8 to 12 degrees or about 10 degrees. Optionally, in other aspects, the desired angle of incidence β can be at least 9 degrees or at least 10 degrees. In a further aspect, and as illustrated in FIG. 10, the pair of light sources that provide the desired off-axis or oblique lights sources can be positioned on opposite sides of the central, coaxial light source.

In this aspect, because the oblique and divergent light beams are not having to assist with coaxial illumination, they can be offset at greater incident angles than prior art illumination systems, which provides for improved depth perception and edge detection. By having oblique and divergent light oblique beams, the illumination system can provide contrast from both sides also improving the overall effect.

In operation, the central or coaxial light source 321 and the remaining pair of off-axis or oblique lights sources 323 use large light emitting surfaces (LES) that are configured to create a less concentrated virtual image on the patient retina. Exemplary LEDs having large light emitting surfaces can include, without limitation, Citizen's Model No. CLU048-1818C4-303H5K2; Citizen's Model No CLU048-1212C4-303H7K4; Bridgelux Inc.'s Model No. BXRC-30E4000-D-73, and the like.

In one aspect, it is desired that each of the central or coaxial light source 321 and the remaining pair of off-axis or oblique lights sources 323 use large light emitting surfaces (LES). Light generated from a conventional "small" point source, such as a filament or smaller LED, generates an undesirably high light intensity that is incident on the patient eye tissue, which can be painful and/or harmful. As identified herein, using a LES LED for each of the central or coaxial light source 321 and the remaining pair of off-axis or oblique lights sources 323 generates a wider, more dispersed, and somewhat diffused light source that provides adequate illumination for the surgical procedure, but generates less incident light energy per measured surface area of the subject tissue, which can provide better patient outcomes and comfort levels.

In various exemplary aspects, it is contemplated that each of the each of the light emitting surfaces LEDs can have a light emitting surface that are greater than about 20.0 mm$^2$, which can create a total light source from the central or coaxial light source 321 and the remaining pair of off-axis or oblique lights sources 323 that is greater than about 60 mm$^2$, or optionally, each of the light emitting surfaces LEDs can have a light emitting surface that are greater than about 30.0 mm$^2$, which can create a total light source of greater from the central or coaxial light source 321 and the remaining pair of off-axis or oblique lights sources 323 that is greater than about 90 mm$^2$. Optionally it is contemplated that each of the each of the light emitting surfaces LEDs can have a light emitting surface that are greater than about 35.0 mm$^2$, which can create a total light source of from the central or coaxial light source 321 and the remaining pair of off-axis or oblique lights sources 323 that is greater than about 105 mm$^2$, or optionally, each of the light emitting surfaces LEDs can have a light emitting surface that are greater than about 38.5 mm$^2$, which can create a total light source from the central or coaxial light source 321 and the remaining pair of off-axis or oblique lights sources 323 that is greater than about 115 mm$^2$.

In a further optional aspect, each of the light emitting surfaces LEDs can have a light emitting surface that are sized to create a total light source from the central or coaxial light source 321 and the remaining pair of off-axis or oblique lights sources 323 that is between about 80 to about 140 mm$^2$, and preferably between about 90 to about 130 mm$^2$. Compared to a typical LED or bulb filament that forms a light source in the 10 mm$^2$ or less, the light sources used in the illumination system help to reduce patient stress and photophobia. In an additional aspect, large light emitting surfaces LEDs used in the illumination system also generate a more diffused light coming from different angles that are not collimated or focused such as the light used in prior art illumination systems.

Each of the large light emitting surfaces LEDs used in the illumination system comprise a plurality of individual LEDs arranged in an array. For example, and without limitation, the plurality of individual LEDs arranged in an array can be greater than 50 individual LED point sources, or greater than 100 individual LED point sources. This results in a light source that provides for a plurality of less intense individual point sources that are configured to create a plurality of diffused multiple dispersed light rays.

In this aspect, the individual LEDs forming the respective large light emitting surfaces LEDs can allow for color adjustment of the generated light beam. In this aspect, because of the large number of individual LED point sources that form the large array, certain groups of LEDs can be of a certain color. Further, it is contemplated that selective groups of individual LED point sources can be independently controlled to control the overall color effect. For example, selective groups of individual LED point sources can be independently controlled off-on and/or bright-dim, to control overall color effect. Thus, the user could adjust color temperature of the light sources via an interface to allow the user to scale the desired color temperature to a desired level.

Figure 17:
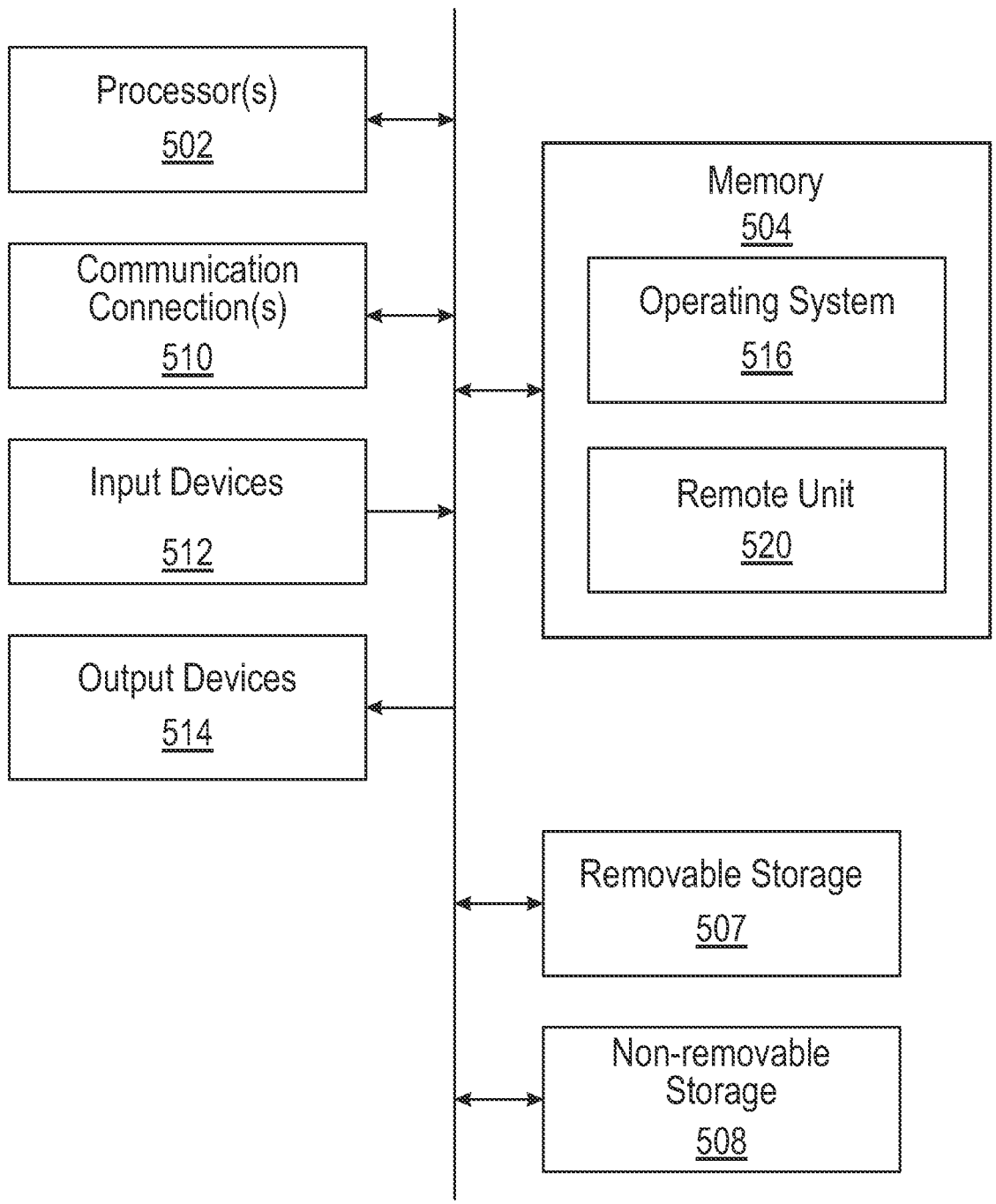
FIG. 17 schematically shows a control system for the operation of the surgical microscope system.

In one aspect and referring to FIG. 17, the head unit microscope assembly 20 is configured to house a control subsystem 500 for the surgical microscope system. Thus, in this exemplary aspect, it is contemplated that the head unit microscope assembly 20 can be configured to contain the electronic controls, computer systems, programing, etc. necessary for operation of the head unit microscope assembly. Thus, in this aspect, it is contemplated that the control subsystem 500 of the head unit microscope assembly 20 can include a processing system having at least one processor 502 and at least one memory 504, which can be coupled to a volatile or non-volatile memory containing a database for storing information related to the operation of the surgical microscope system. The memory 504 being configured to contain instructions that, when executed by the processor, are operative to perform the essential, recommended and/or optional functions in various embodiments of the surgical microscope system 10 described herein. Is this aspect, the control subsystem 500 has at least one memory that is configured to store program instructions such that, in operation, the at least one memory of the control subsystem 500 is configured to store program instructions that, when executed, cause the surgical microscope assembly to perform the required operations. Optionally, if the floor stand that the head unit microscope assembly is retrofitted thereto contains operational electronics, the head unit microscope assembly can be configured to selectively communicate with the floor stand electronics.

To regulate the operation of the surgical microscope system 10, the control subsystem 500 can include input devices 512 (such as sensors) and output devices 514 (such as actuators) that are operatively coupled to the processor(s) 502. The control subsystem 500 includes a memory 504 that is in communication with the processor(s) 502 and may also include other features such as limiters, conditioners, filters, format converters, or the like which are not shown to preserve clarity. One or more operator input devices 512 can also be coupled to the controller 502 to provide corresponding operator input to adjust/direct one or more aspects of surgical microscope system operation. Exemplary input devices can include, without limitation, a keyboard, mouse, pen, voice input device, gesture input device, foot control device, and/or touch input device, or any other suitable input device. The control subsystem 500 can further include one or more output devices 514 that are coupled to the controller 502, such as a display, printer, and/or speakers, or any other suitable output device. In other embodiments, however, computer-readable communication media may include computer-readable instructions, program modules, or other data transmitted within a data signal, such as a carrier wave, or other transmission. Optionally, the control subsystem 500 can also include an audible alarm, warning light(s), or the like (not shown) can also be coupled to the controller 502 that each respond to various output signals from controller 502.

In additional detail, the control subsystem 500 is configured for implementing certain systems and methods for operating a surgical microscope system in accordance with certain embodiments of the disclosure. The processor(s) 502 is configured to execute certain operational aspects associated with implementing certain systems and methods described herein. The processor(s) 502 can be implemented and operated using appropriate hardware, software, firmware, or combinations thereof. Software or firmware implementations may include computer-executable or machine-executable instructions written in any suitable programming language to perform the various functions described. In some examples, instructions associated with a function block language may be stored in the memory 504 and executed by the processor(s) 502.

As one will appreciate, the memory 504 can be used to store program instructions, such as instructions for the execution of the methods illustrated herein or other suitable variations. The memory 504 can include, but is not limited to, an operating system 516 and one or more application programs or services for implementing the features and embodiments disclosed herein. Such applications or services may include remote units 520, such as the remote viewing assembly described below, for executing certain systems and methods for controlling operation of the surgical microscope system (e.g., semi- or full-autonomously controlling operation of the remote viewing assembly.

The instructions are loadable and executable by the processor(s) 502 as well as to store data generated during the execution of these programs. Depending on the configuration and type of the control subsystem 500, the memory 504 may be volatile (such as random-access memory (RAM)) and/or non-volatile (such as read-only memory (ROM), flash memory, etc.). In some embodiments, the memory devices may include additional removable storage 507 and/or non-removable storage 508 including, but not limited to, magnetic storage, optical disks, and/or tape storage. The disk drives and their associated computer-readable media may provide non-volatile storage of computer-readable instructions, data structures, program modules, and other data for the devices. In some implementations, the memory 504 includes multiple different types of memory, such as static random-access memory (SRAM), dynamic random access memory (DRAM), or ROM.

The memory 504, the removable storage 507, and the non-removable storage 508 are all examples of computer-readable storage media. For example, computer-readable storage media may include volatile and non-volatile, removable and non-removable media implemented in any method or technology for storage of information such as computer-readable instructions, data structures, program modules or other data. Additional types of computer storage media that may be present include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile discs (DVD) or other optical storage, magnetic cassettes, magnetic tapes, magnetic disk storage or other magnetic storage devices, or any other medium which may be used to store the desired information and which may be accessed by the devices. Combinations of any of the above should also be included within the scope of computer-readable media.

The control subsystem 500 can also include one or more communication connections 510 that may allow a control device (not shown) to communicate with devices or equipment capable of communicating with the control subsystem 500. Connections may also be established via various data communication channels or ports, such as USB or COM ports to receive cables connecting the control subsystem 500 to various other devices on a network. In one embodiment, the control subsystem 500 can include Ethernet drivers that enable the control subsystem 500 to communicate with other devices on the network. According to various embodiments, communication connections 510 may be established via a wired and/or wireless connection on the network.

It is contemplated that the control subsystem 500 can be comprised of one or more components that may be configured as a single unit or distributed among two or more units. The processor(s) 502 and/or the memory 504 can be combined in a common integrated circuit, defined by separate circuitry, or comprised of one or more other component types of a solid state, electromagnetic, optical, or different variety as would occur to those skilled in the art. The control subsystem 500 may include analog circuitry, digital circuitry, and/or a hybrid combination of both of these types. In one aspect, the control subsystem 500 is configurable for to reside within the head unit microscope assembly.

In one form, the control subsystem 500 is of the programmable variety that executes algorithms and processes data in accordance with operating logic that is defined by programming instructions (such as software or firmware). Alternatively, and/or additionally, operating logic for the control subsystem 500 is at least partially defined by hardwired logic or other hardware. In one particular form, the control subsystem 500 can be configured to operate as a Full Authority Digital Engine Control (FADEC); however, in other embodiments it may be organized/configured in a different manner as would occur to those skilled in the art. As exemplarily illustrated in the flowcharts of the present application, it is contemplated the control subsystem 500 is programed to execute algorithms and to process data in accordance with the operating logic that is defined by programming instructions and or steps illustrated in the associated figures.

It is further contemplated that the control subsystem 500 may include one or more industrial control systems (ICS), such as, for example, Supervisory Control and Data Acquisition (SCADA) systems, distributed control systems (DCS), and programmable logic controllers (PLCs), or other suitable control systems and/or control features without departing from the disclosure.

The control subsystem 500 can also include a number of sensors to provide input to controller 502. Some of these exemplary inputs are illustrated in the figures and include sensors or inputs generated by the respective XY directional stage 220, tilt drive 230, focus drive 240; microscope subassembly 300, and/or an illumination system 320.

Remote Viewing Assembly

Figure 19:
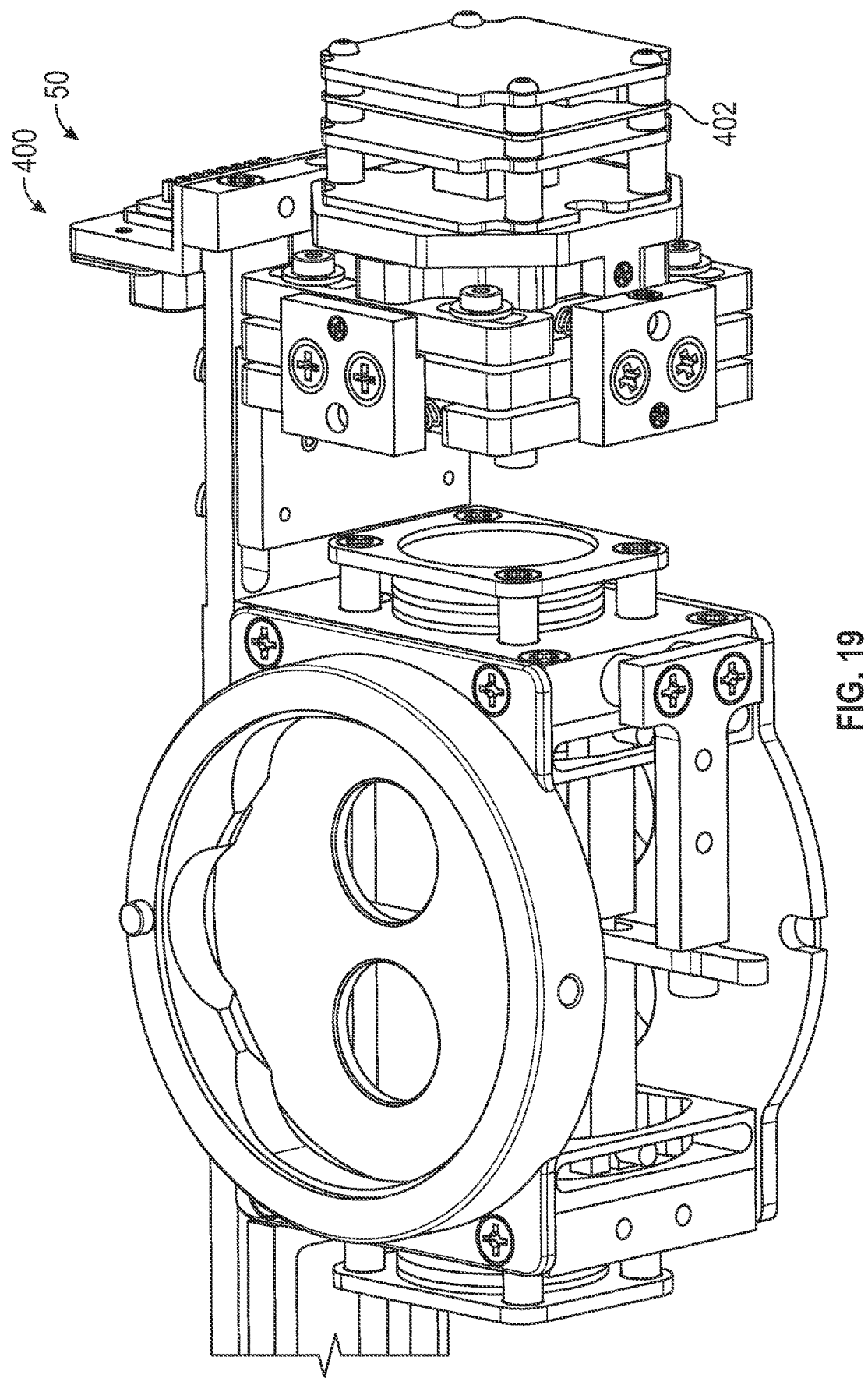
FIG. 19 schematically illustrates an example of a remote viewing assembly that can be used in the exemplary surgical microscope system.
Figure 20:
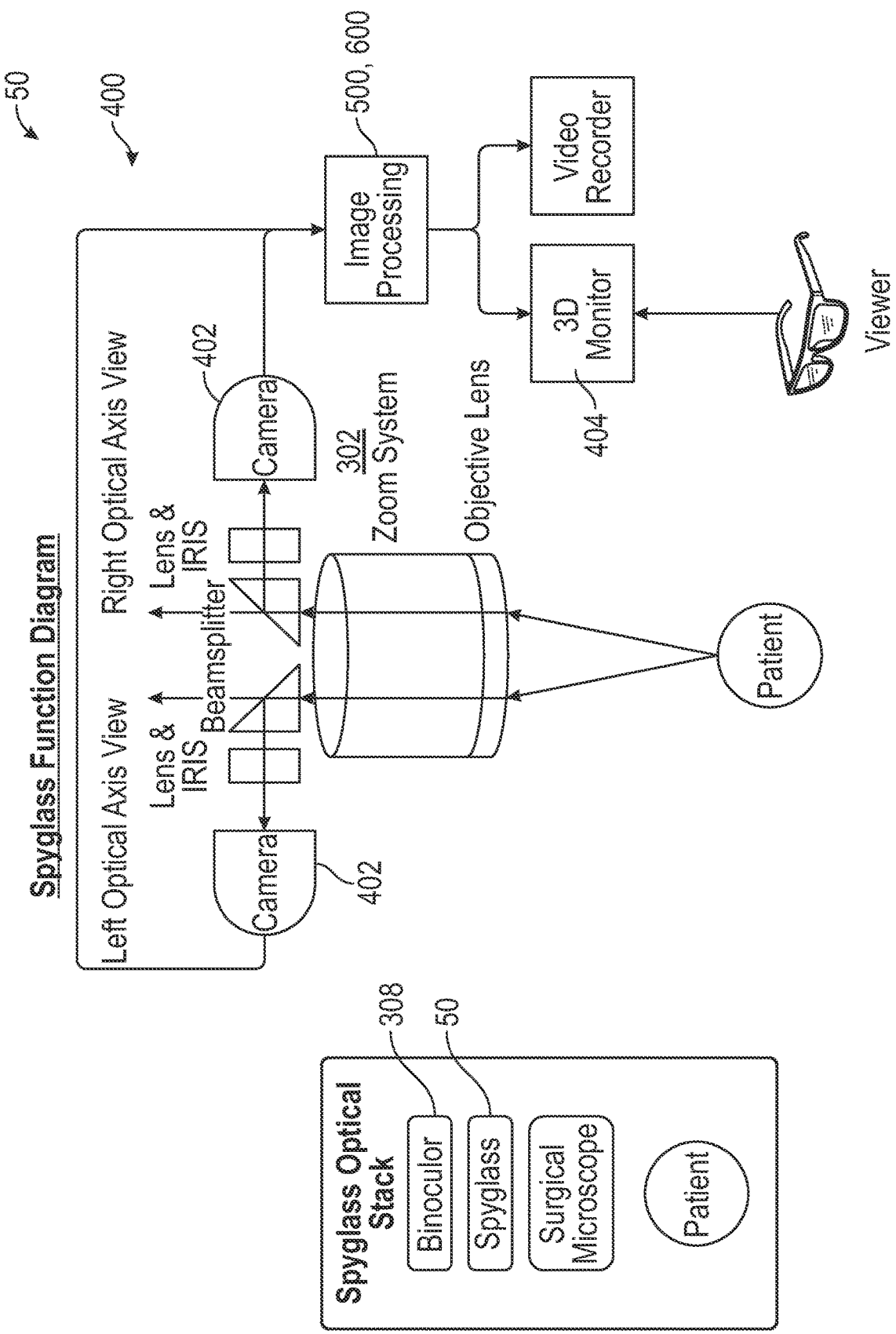
FIG. 20 illustrates a schematic function diagram, in an embodiment, of the remote viewing assembly of FIG. 19.

Referring to FIGS. 19-20, the remote viewing assembly 50 is in operative communication with the head unit microscope assembly 20 and can comprise a camera assembly 400 that is mountable between the binocular optics module 308 and the zoom optics module 302. In this aspect, the camera assembly 400 comprises an opposed pair of high resolution cameras 402 that are configured to produce a left and right "view" of the image in the microscope, which are subsequently combined and displayed on a remote 3D monitor 404. In one exemplary aspect, and not intended to be limiting, each camera can comprise a ⅓ inch CCD video camera. Exemplary cameras can include, without limitation, Sony's Model Nos. MCC-1000MD and MCC-1000MD; Panasonic's Model No. GP-UH532; Hitachi's Model No. HV-UHD301; Omron Sentech Co, Ltd. Model No. STC-HD213DV camera, and the like.

A user can use passive 3D glasses to perceive the displayed 3D image. Alternatively, the remote viewing assembly 50 is configured to allow for the user to use the conventional binocular view of the microscope to view the image concurrently with the view of the image being presented on the remote 3D monitor.

The respective opposed pair of high resolution cameras 402 are each individually adjustable along their individual X, Y, and Z axis and allow for rotational adjustment of the respective cameras to allow the desired alignment of the respective left and right images.

Figure 21:
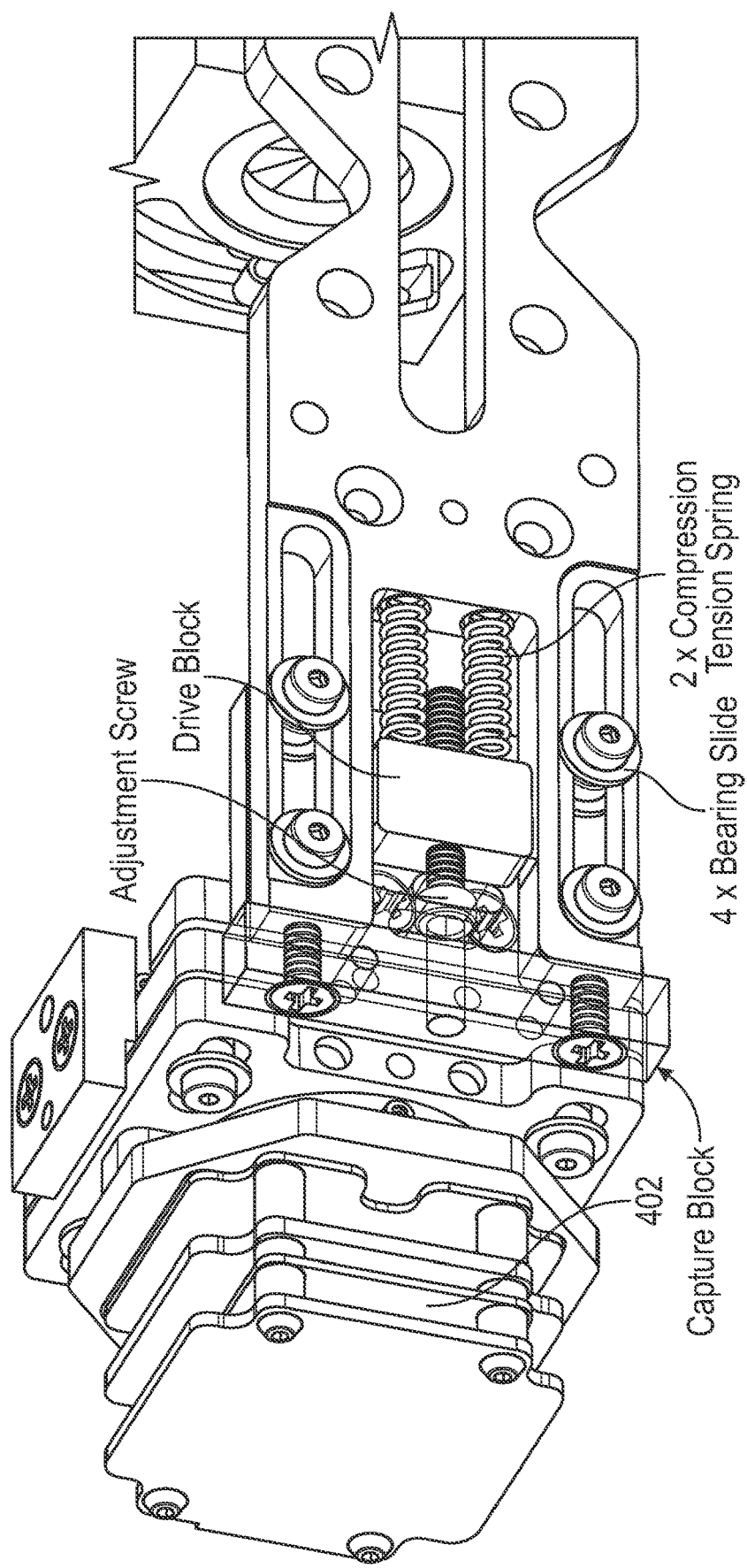
FIG. 21 schematically illustrates an example of a Z axis assembly of the remote viewing assembly that can be used in the exemplary surgical microscope system.
Figure 22:
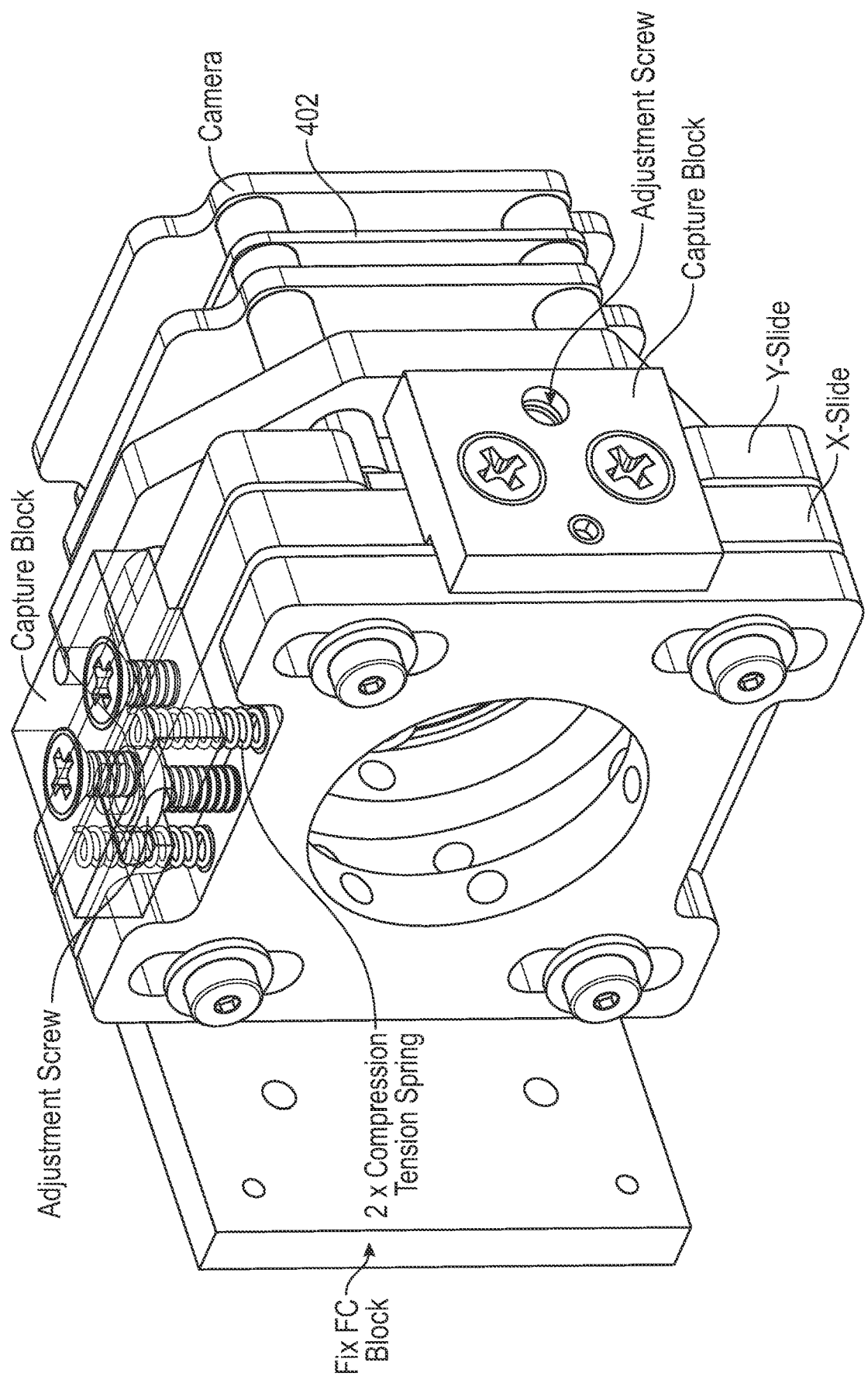
FIG. 22 schematically illustrates an example of a XY axis assembly of the remote viewing assembly that can be used in the exemplary surgical microscope system.
Figure 26:
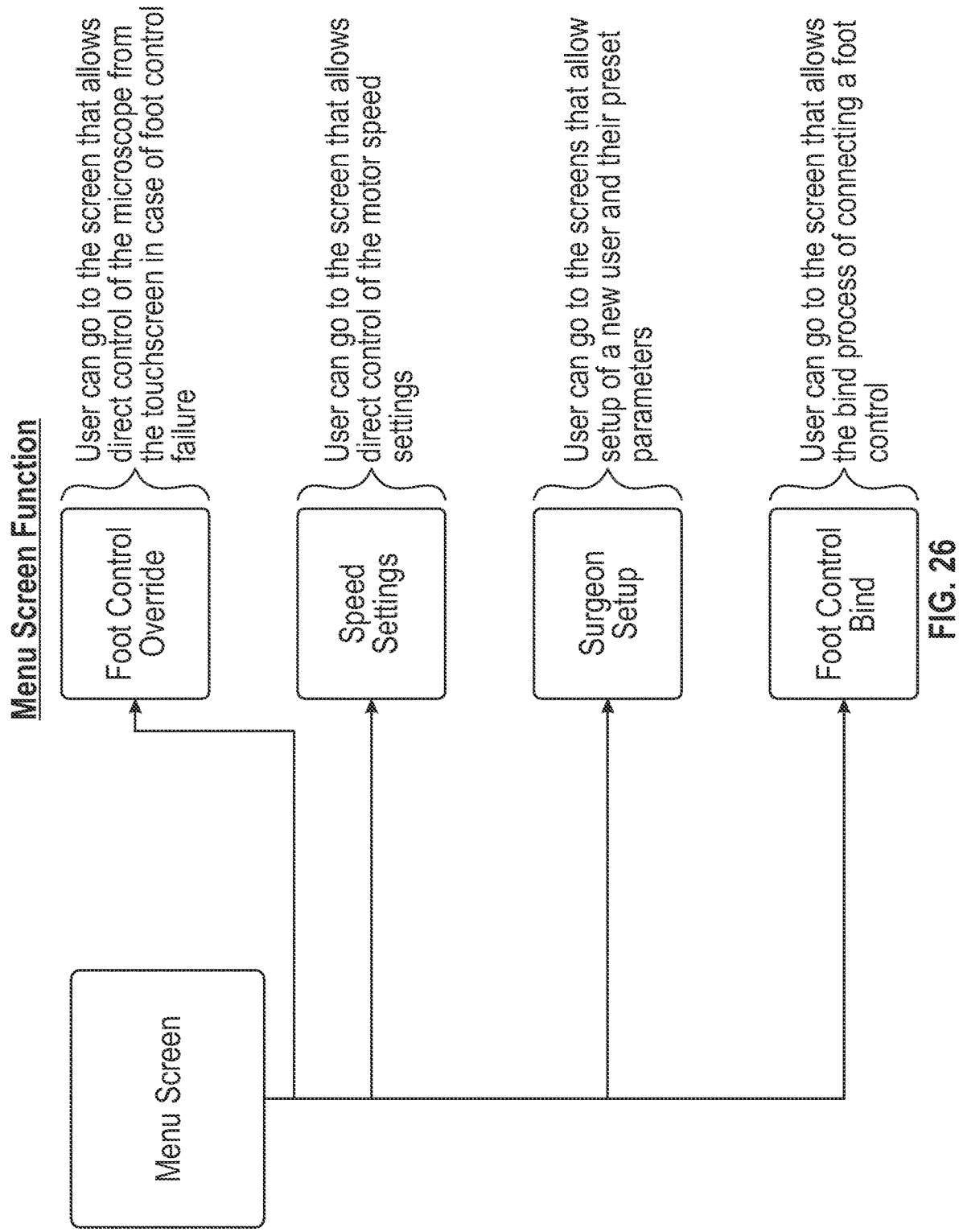
FIG. 26 illustrates a process flow, in an embodiment, of home screen controls for the surgical microscope system.
Figure 27:
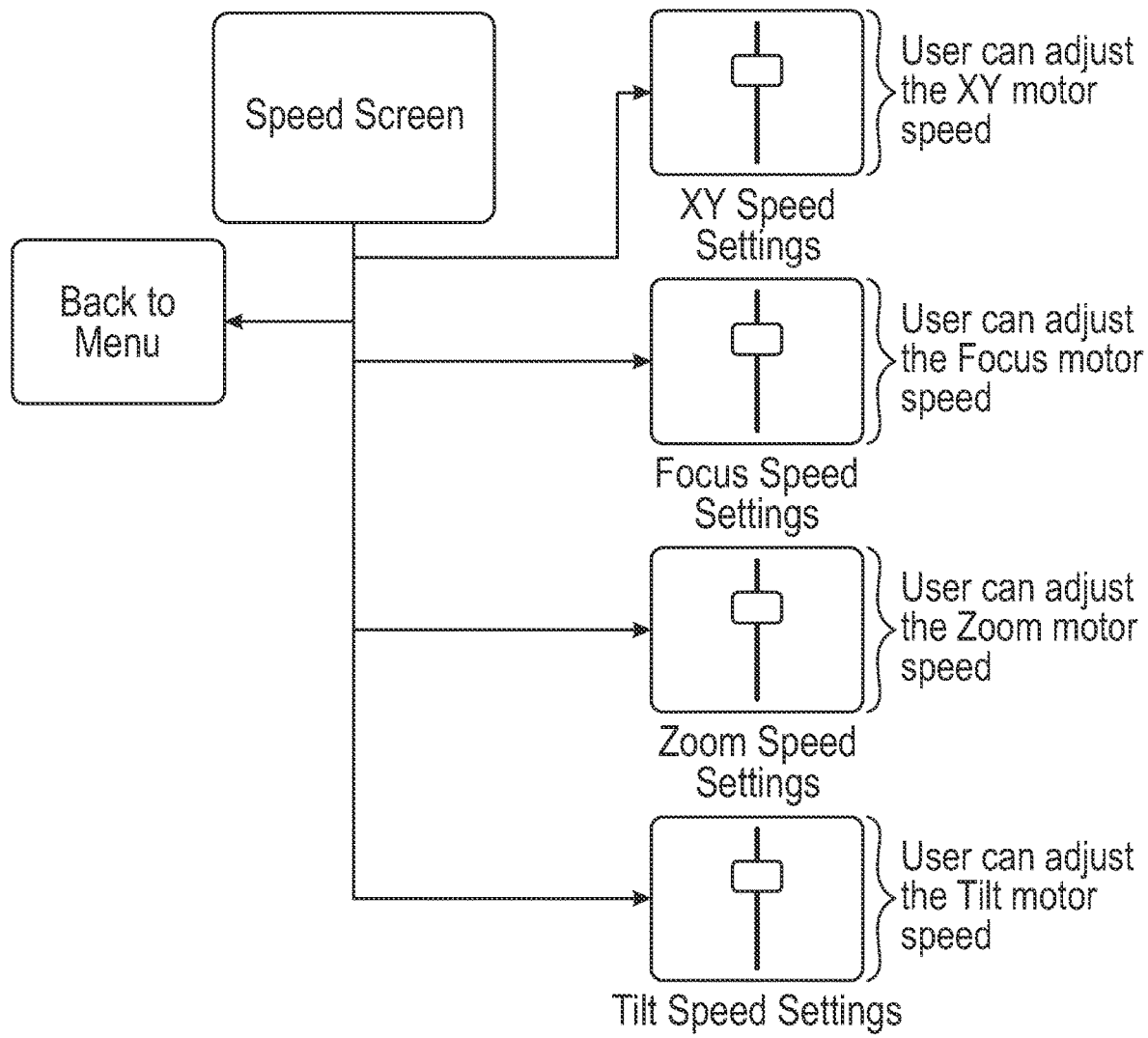
FIG. 27 illustrates a process flow, in an embodiment, of home screen controls for the surgical microscope system, showing "speed" selections to allow a user to select stored system settings.
Figure 28:
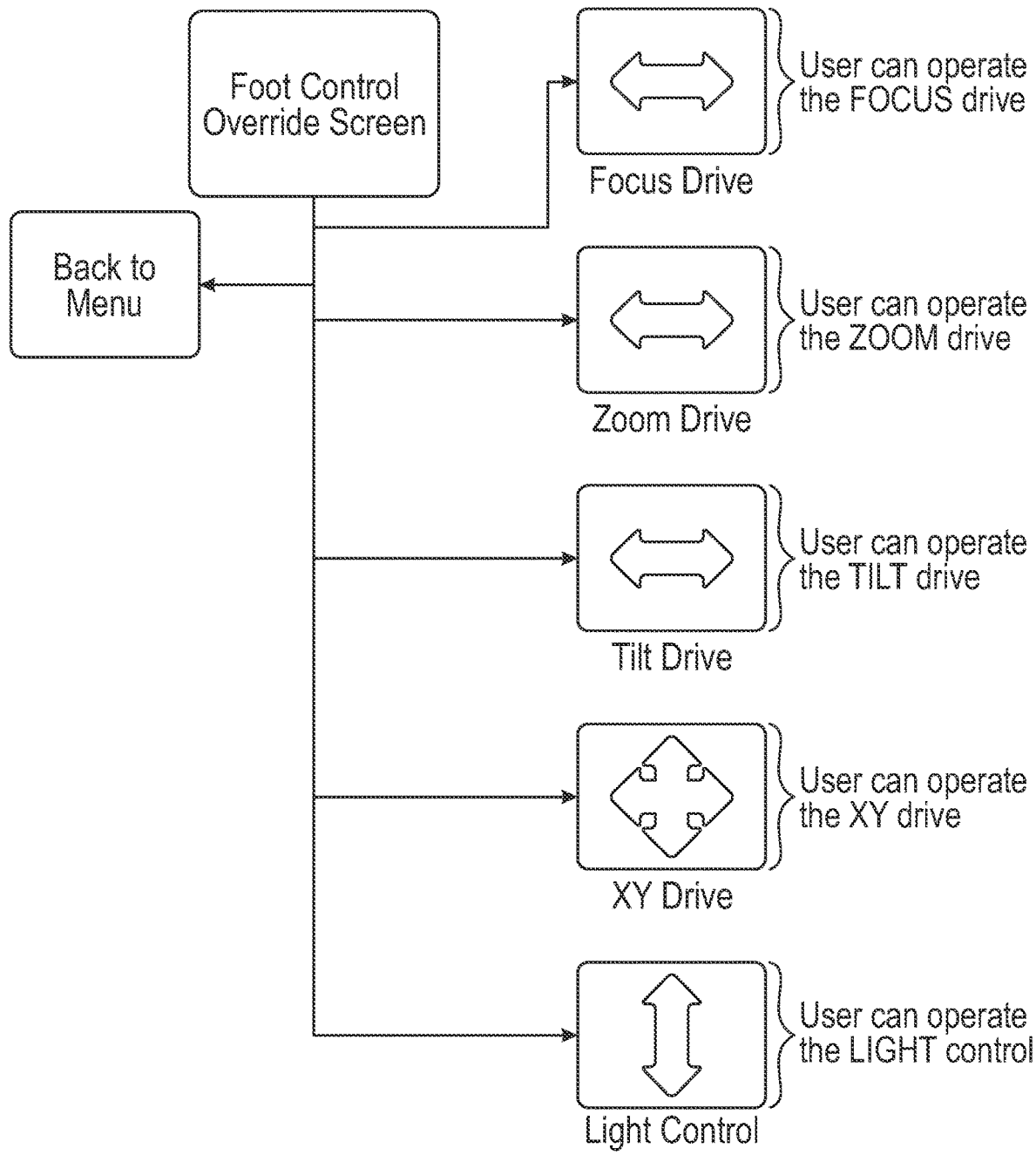
FIG. 28 illustrates a process flow, in an embodiment, of override home screen controls for the surgical microscope system.
Figure 29:
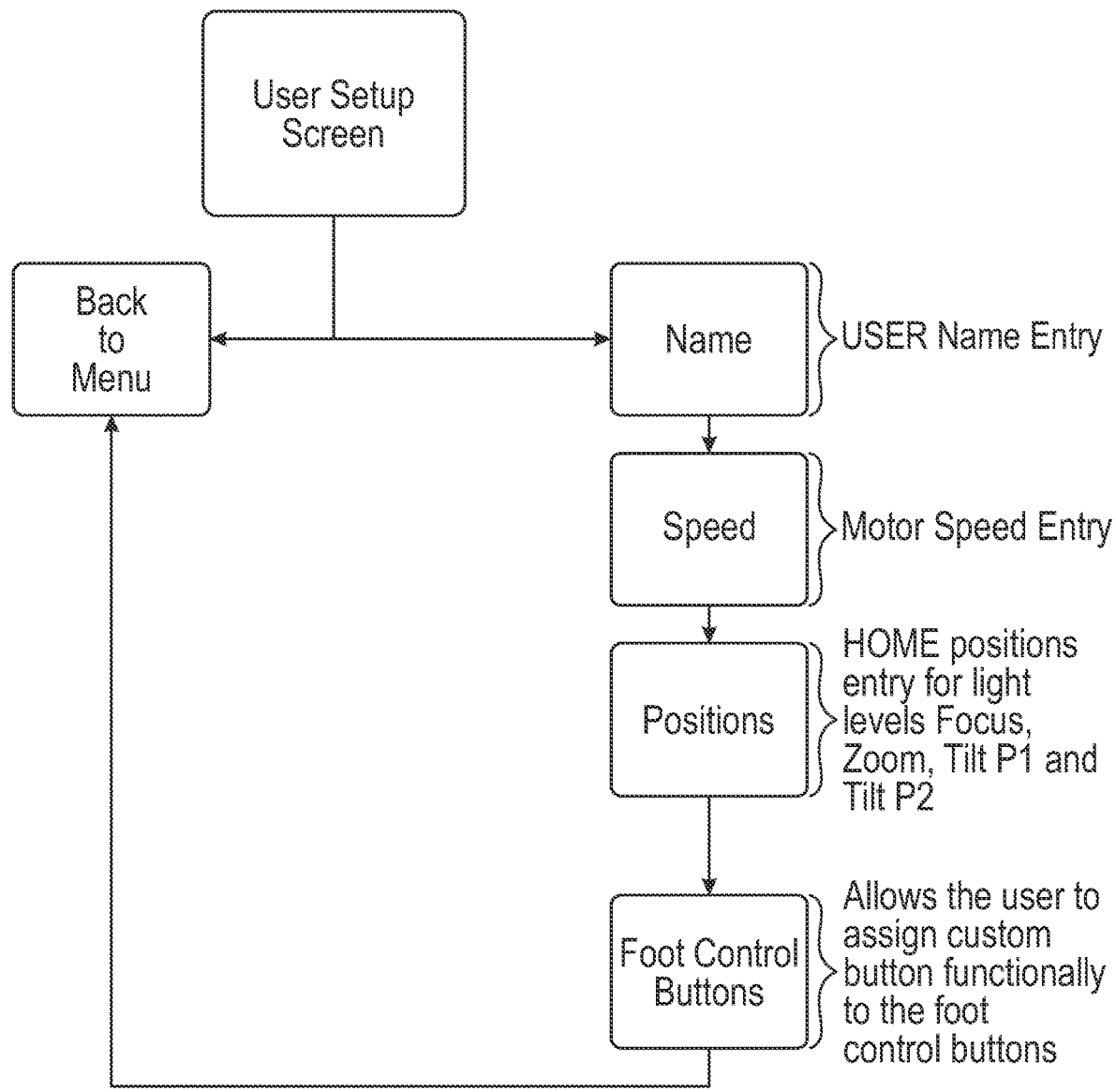
FIG. 29 illustrates a process flow, in an embodiment, of user setup home screen controls for the surgical microscope system.

Referring now to FIG. 21, for each high resolution camera 402, the Z axis can be adjusted by the actuation of a Z axis assembly in which the movement of a screw axially move a drive block, dependent upon the direction the screw is rotated. At least one spring is provided that provides a desired level of compression against the spring to minimize any slack or play in the mechanics. Similarly, and referring to FIG. 26, the respective X and Y axis can be adjusted by the actuation of a XY axis assembly in which the movement of respective screws axially move respective drive blocks, dependent upon the direction the respective screws are rotated. At least one spring is provided for each respective X and Y axis to provide a desired level of compression against the spring to minimize any slack or play in the mechanics. As shown, the XY axis assembly includes a fixed block that is configured to attach to the drive block of the Z axis assembly.

Figure 23:
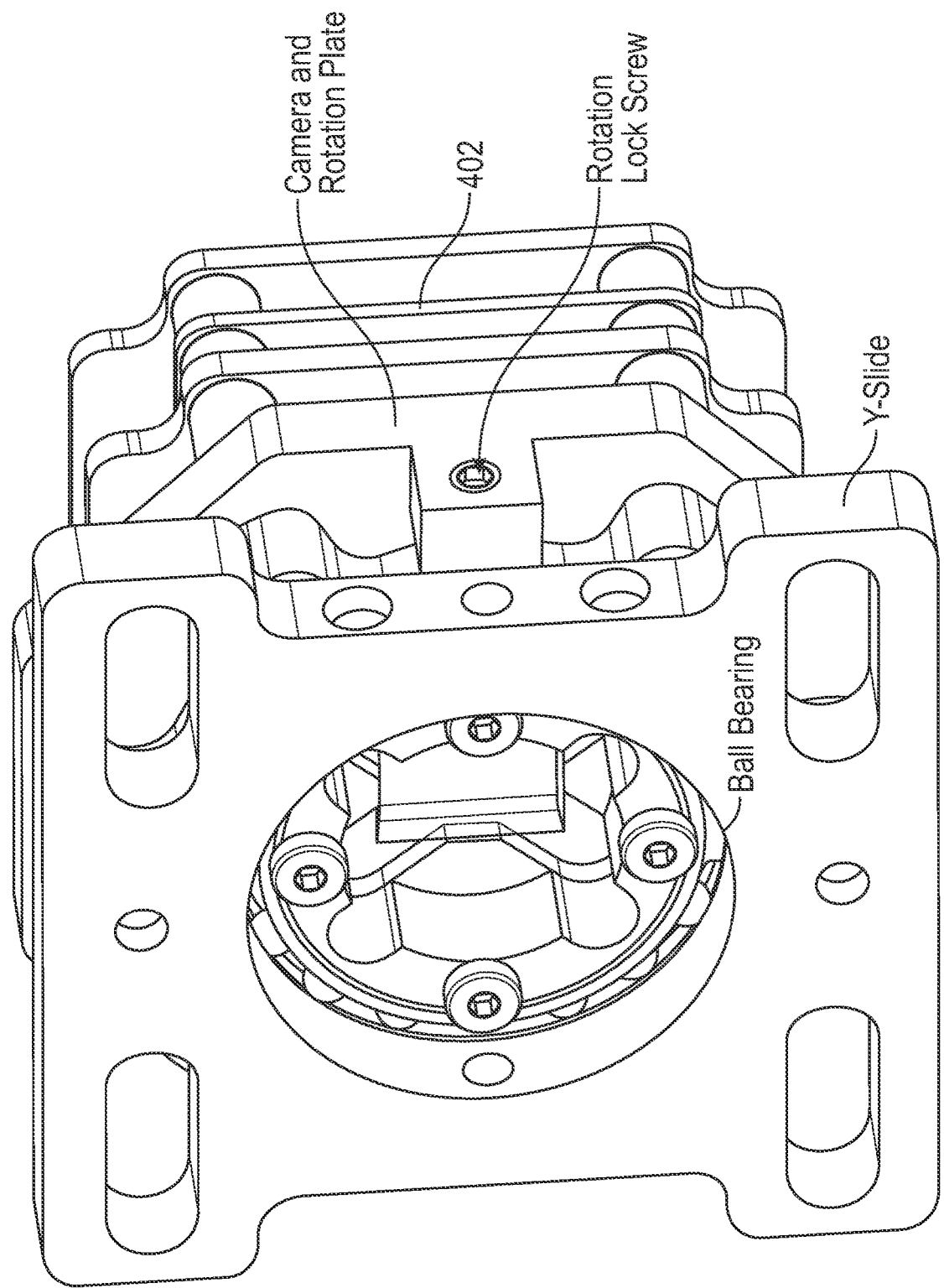
FIG. 23 schematically illustrates an example of a rotation assembly of the remote viewing assembly that can be used in the exemplary surgical microscope system.
Figure 24:
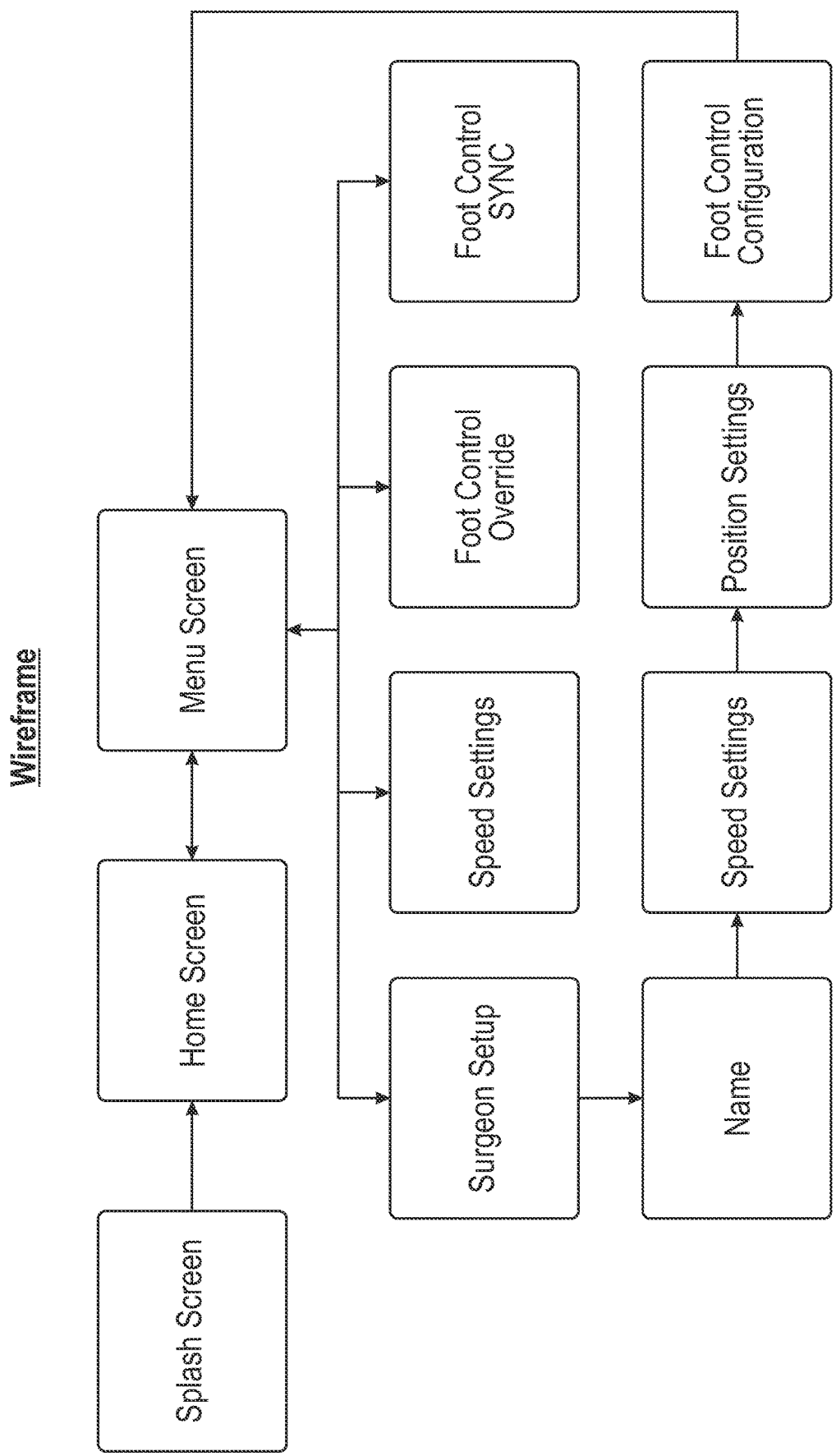
FIG. 24 illustrates a process flow, in an embodiment, of home screen operation for the surgical microscope system.
Figure 25:
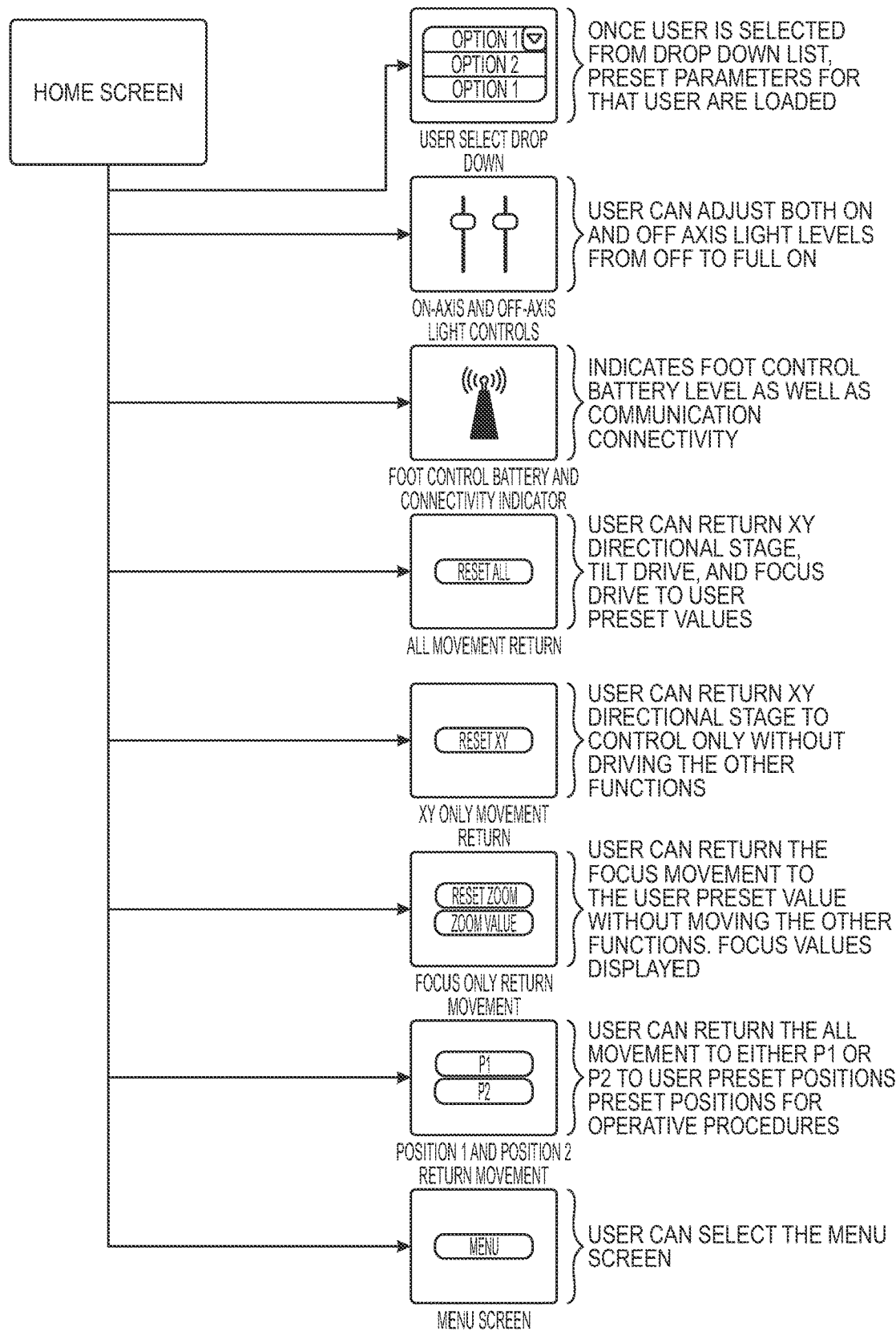
FIG. 25 illustrates a process flow, in an embodiment, of home screen controls for the surgical microscope system.

Further, as shown in FIG. 23 and with respect to the desired rotational adjustment of the respective cameras, the Y slide of the XY assembly is fixed to the outer race of a ball bearing. In this aspect, a camera 402 and rotation plate are configured to be connected to the inner race of the ball bearing. In operation, when the desired rotational adjustment of the camera and rotation plate is accomplished, a rotation lock screw can be tightened to fix the camera and rotation plate relative to the operably coupled Y slide.

In one aspect, the remote viewing assembly 50 can use the control system 500 of the surgical microscope system to operate and or control the remote viewing assembly. Thus, in this exemplary aspect, it is contemplated that the head unit microscope assembly can be configured to contain the electronic controls, computer systems, programing, etc. necessary for operation of the head unit microscope assembly and the remote viewing assembly.

Figure 18:
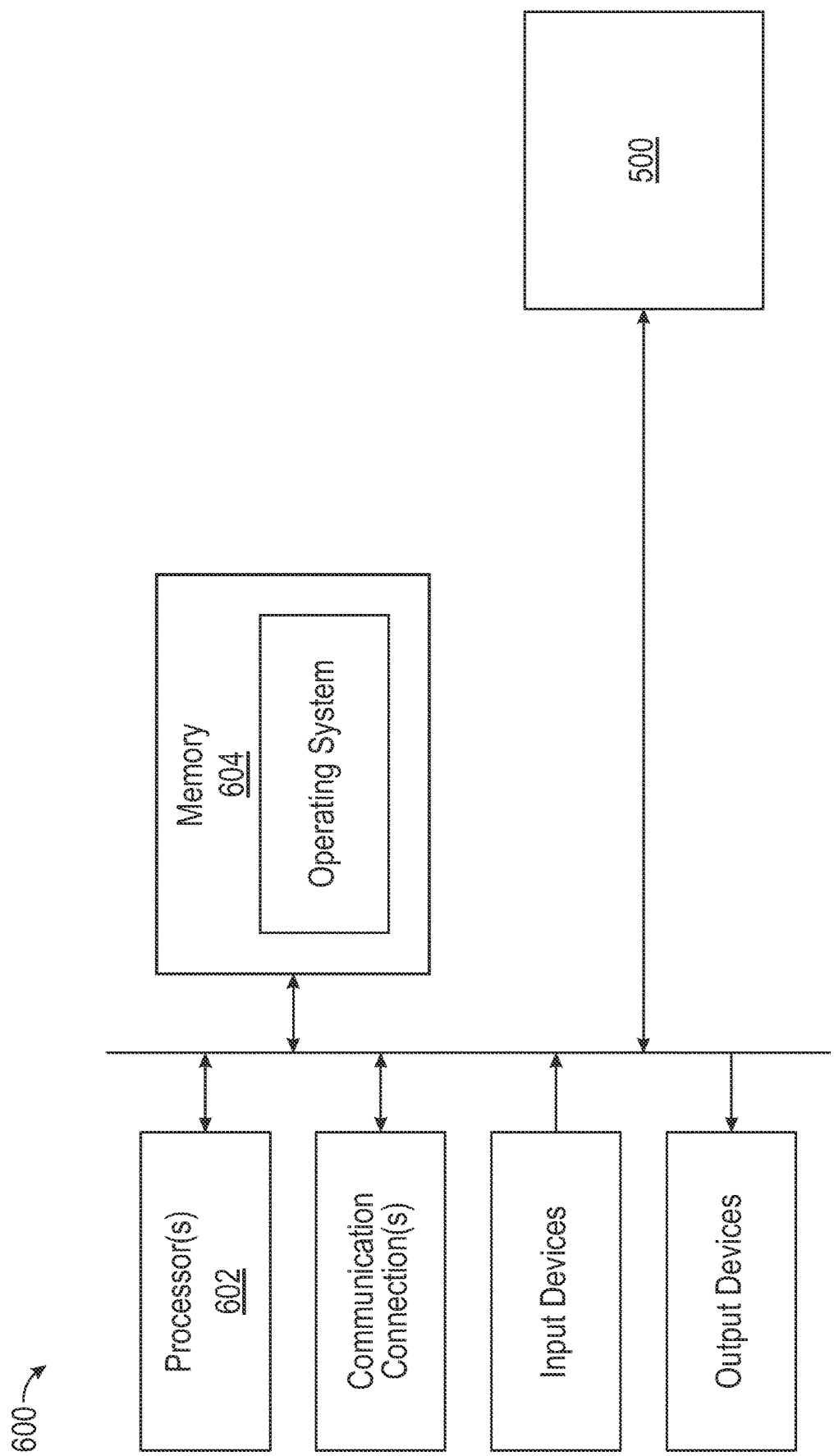
FIG. 18 schematically shows a control system for the operation of a remote viewing assembly that can be used in the exemplary surgical microscope system.

Optionally, and as shown in FIGS. 18 and 20, the remote viewing assembly 50 can be configured to house a control subsystem 600 that is separable from the control subsystem 500 of the surgical microscope system. Thus, in this exemplary aspect, it is contemplated that the remote viewing assembly 50 can be configured to contain the electronic controls, computer systems, programing, etc. necessary for operation of the remote viewing assembly. Thus, in this aspect, it is contemplated that the control subsystem 600 of the remote viewing assembly can include a processing system having at least one processor 602 and at least one memory 604, which can be coupled to a volatile or non-volatile memory containing a database for storing information related to the operation of the surgical microscope system. The memory containing instructions that, when executed by the processor, are operative to perform the essential, recommended and/or optional functions in various embodiments of the remote viewing assembly described herein. Is this aspect, the processing system has at least one memory that is configured to store program instructions such that, in operation, the at least one memory of the processing system is configured to store program instructions that, when executed, cause the surgical microscope assembly to perform the required operations.

In a further aspect, it is contemplated that the respective opposed pair of high-resolution cameras 402 can be adjusted along their respective individual X, Y, and Z axis, and rotational axis to allow the desired alignment of the respective left and right images via an automated system. In one aspect, such an automated system could include the use of a feducial or special target for the respective opposed pair of high-resolution cameras. Then the processor of the control subsystem 600 would analyze the images received from the respective cameras and instruct actuators or electrical motors, instead of the previously described screws, to affect the desired X, Y, and Z axis, and/or rotational axis adjustments.

In operation, a method for such an automated system could include: placing a special target reticle or feducial under the scope in focus at high magnification; centering the target reticle or feducial in the visual field, looking through the binocular optics module 308; initiating an auto-align function on the processor of the control subsystem 600; analyzing the incoming left and right video data streams via the processor of the control subsystem 600; instructing the respective actuators or electrical motors, via the processor of the control subsystem 600, to effect the desired X, Y, and Z axis, and/or rotational axis adjustments while concurrently analyzing the left and right video data streams until the respective target reticle or feducial were aligned to specification and in focus.

Foot Control Assembly

Figure 30:
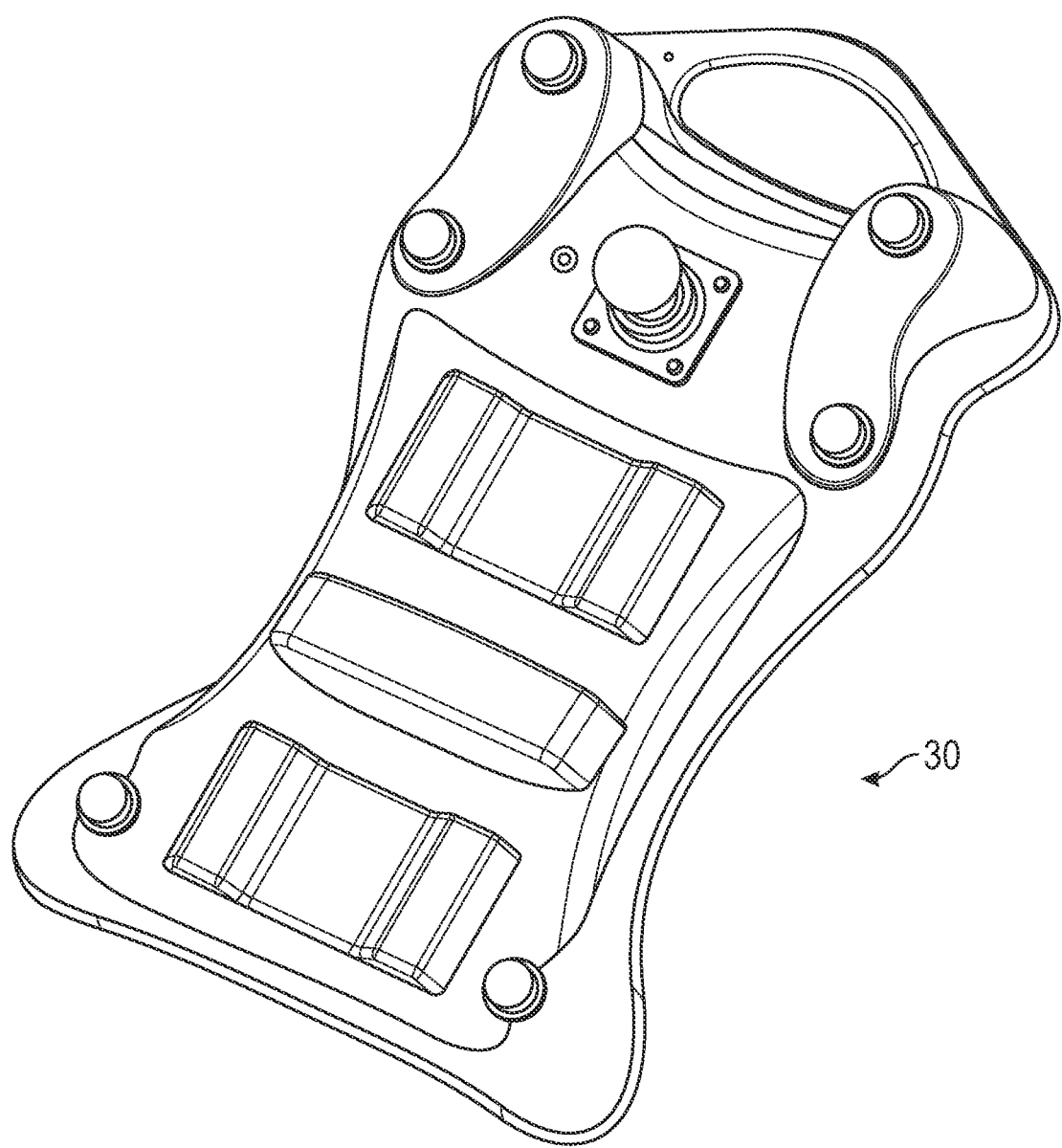
FIG. 30 schematically illustrates an example of a foot control assembly.
Figure 31:
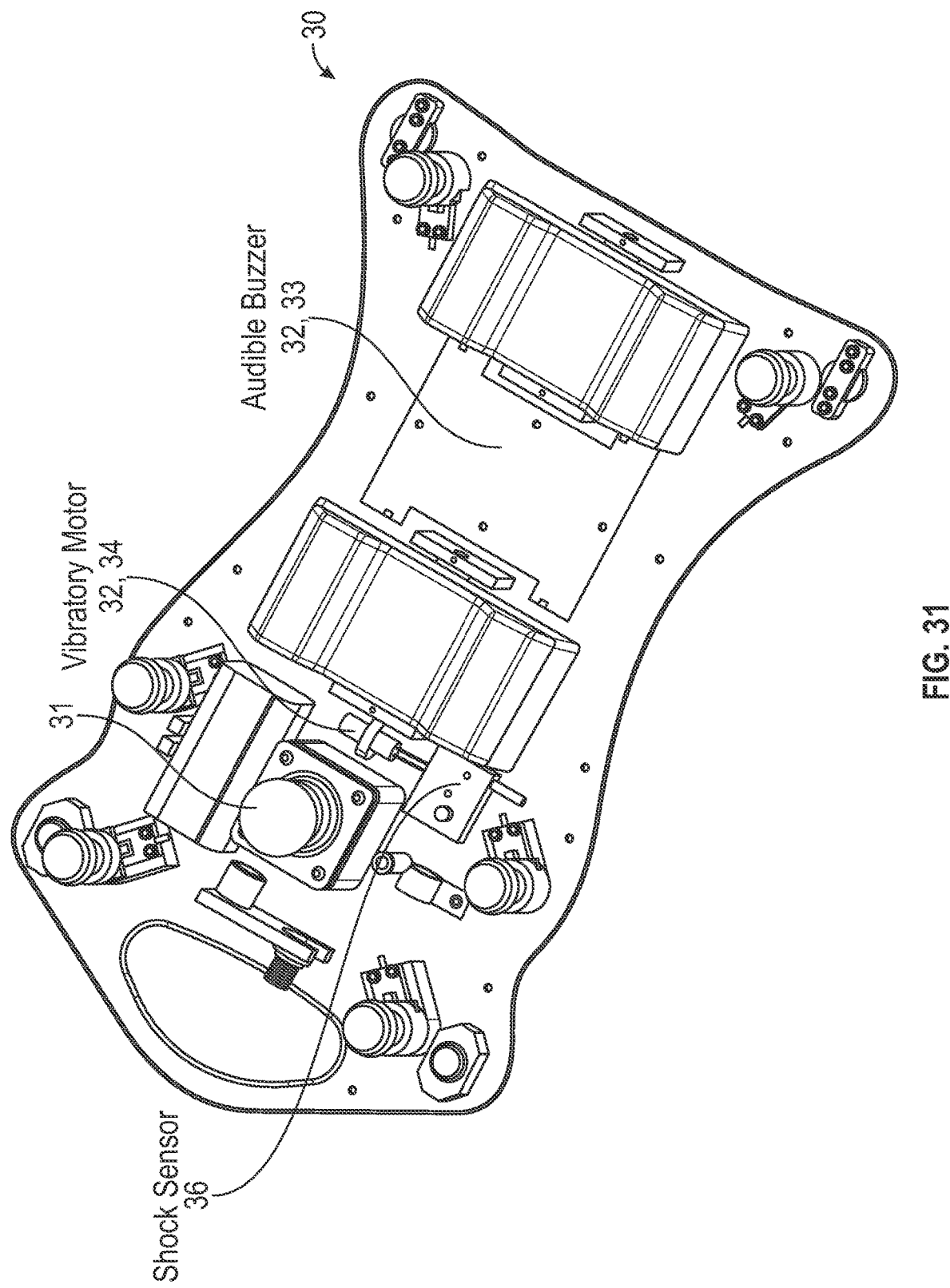
FIG. 31 schematically illustrates exemplary aspects of the foot control assembly of FIG. 30.
Figure 32:
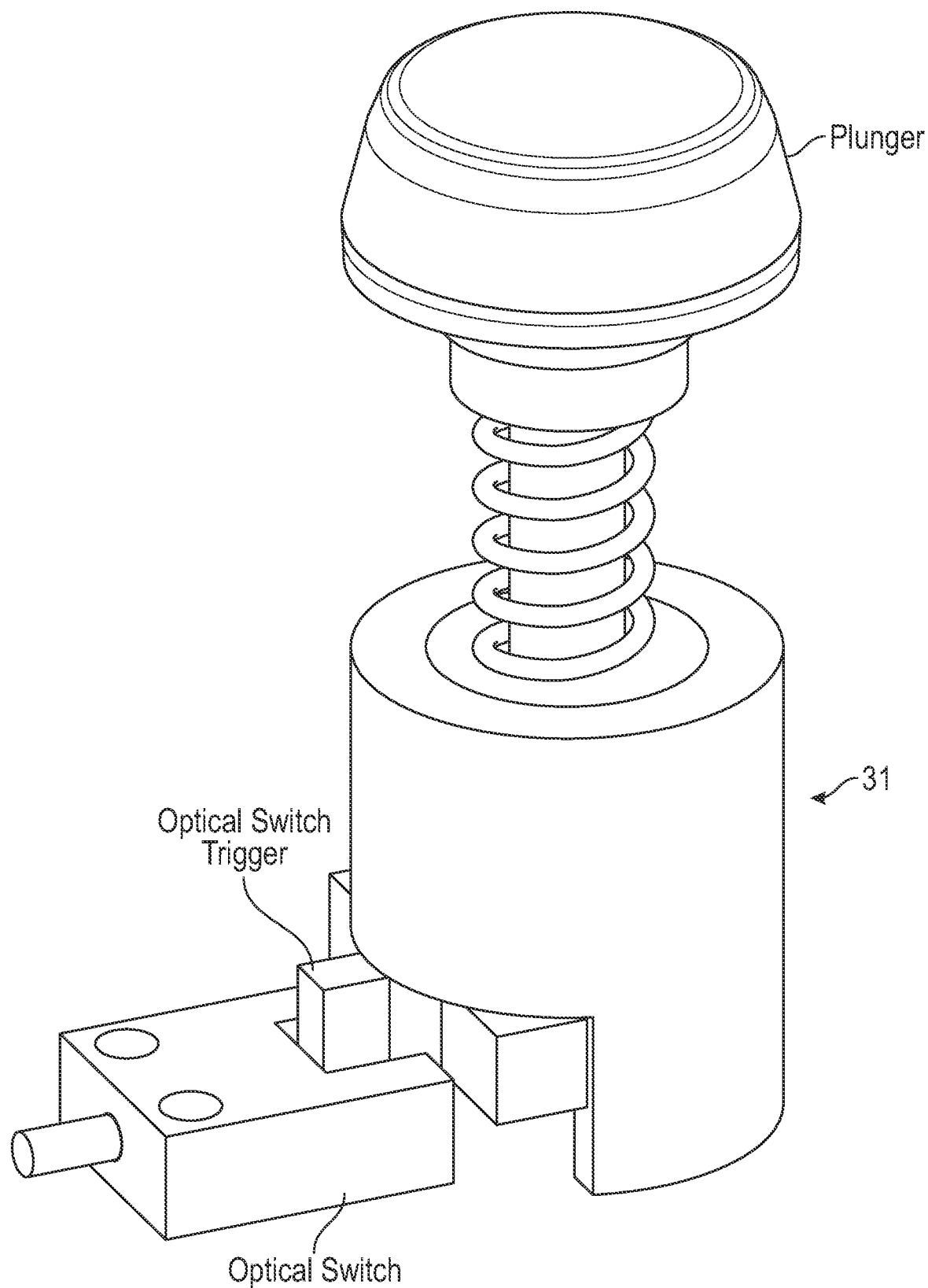
FIG. 32 schematically illustrates an example of an optical switch for use in the foot control assembly of FIG. 31.
Figure 33:
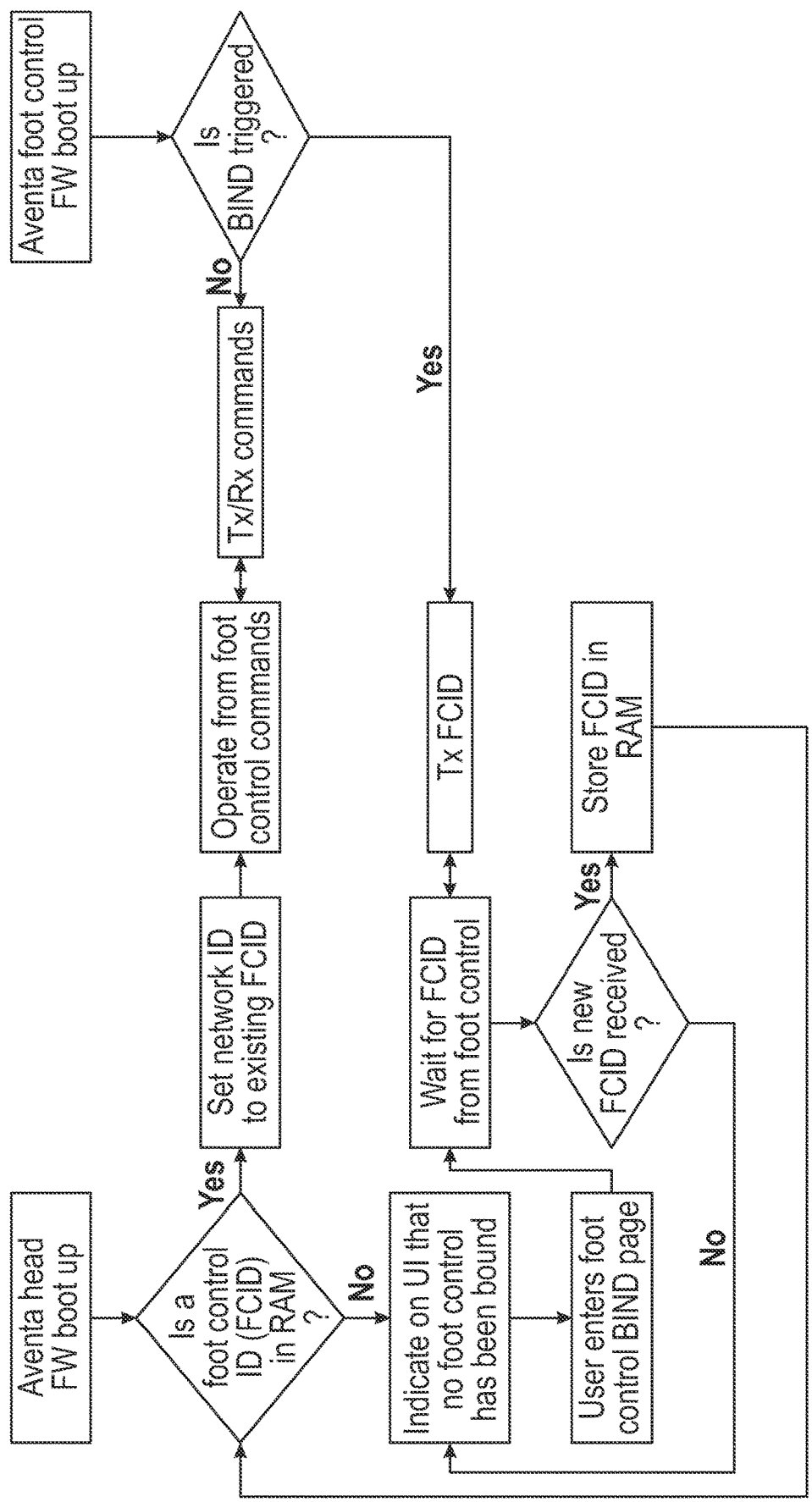
FIG. 33 illustrates a process flow, in an embodiment, for operatively binding the foot control to the heat unit assembly of the surgical microscope system.
Figure 34:
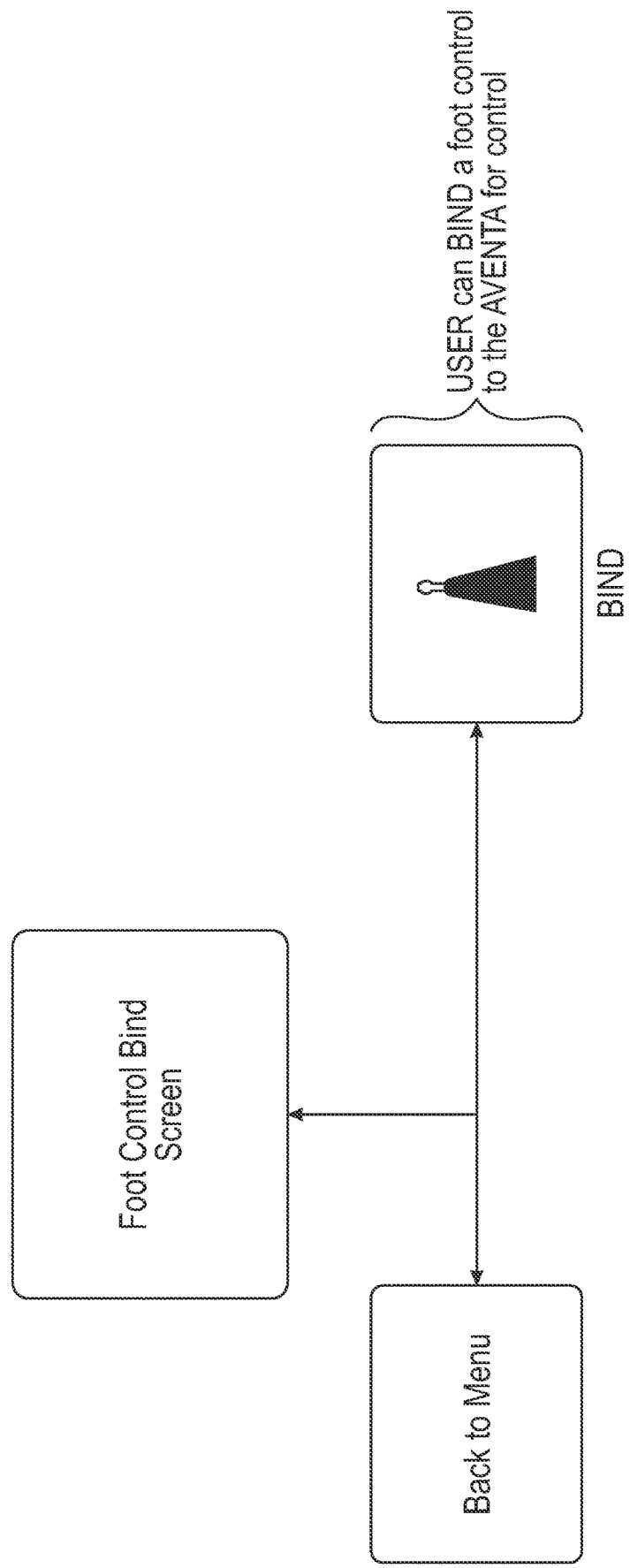
FIG. 34 illustrates a process flow, in an embodiment, of home screen controls for control of the foot control assembly of the surgical microscope system.

In one aspect, and referring to FIGS. 30-32, the foot control assembly 30 can operate as the primary control interface for the head unit microscope assembly 20. In various aspects, the foot control assembly 30 is configured to allow a surgeon to control functions of the head unit microscope assembly 20 with their feet. Since eye surgery is done with the surgeon sitting down, their hands are sterile and holding instruments, the instruments are generally inserted into the patient's eye, it is very undesirable to have to retract the instruments, lay them down, operate the function of the microscope as needed, and then resume surgery. Having to take instruments in and out of the eye incisions excessively does not optimize surgical outcomes for the patient. Also, breaking sterility for the surgeon is a possibility if they have to manipulate some function of the head unit microscope assembly 20. Having a simple remote control via foot actions provides a great way to control features of the head unit microscope assembly 20, such as, for example, XY directional stage 220, tilt drive 230, and/or the focus drive 270 movements, zoom and illumination controls, etc.

In one aspect, it is contemplated that the foot control assembly 30 can comprise a wireless, battery operated device that is configured to reduce cord clutter in an operating room and can further have control switches that are positioned in a conventional surgical control layout. In this aspect, and as shown in FIGS. 31 and 32, it is contemplated that the control switches for the foot control assembly 30 can comprise at least one of hall effect (magnetic) and/or optical switches 31 for increased surgical reliability.

Referring to FIG. 31, it is further contemplated that the foot control assembly 30 can comprise at least one alarm module 32. In this aspect, the alarm module 32 can be configured to activate upon when one or more of the XY directional stage 220, tilt drive 230, and/or the focus drive 270 approaches or reaches a range of movement limitation, an "end of excursion" limitation, for the respective XY directional stage 220, tilt drive 230, and/or a focus drive 270. For example, in this aspect it is contemplated that, if one or more of the pair of linear potentiometers senses that the operational movement of the XY directional stage 220 is approaching or has reached a range of movement limitation of the XY directional stage 220, such that further movement of the XY directional stage 220 would be prohibited along a desired X and Y axis, the control subsystem 500 of the head unit microscope assembly 20 would send a signal to actuate the alarm module 32 of the foot control assembly 30. In this example, the actuated alarm module 32 would act to inform the surgeon that they have reached the limit of the range of movement of the XY directional stage 220 along at least one of the respective X and Y axis of movement.

Similarly, if at least one rotational potentiometers 263 of the tilt drive 230 coupled to the respective first and second gears senses that the operational movement of the tilt drive 230 is approaching or has reached a range of movement limitation of the tilt drive 230, such that further rotational movement of the drive member relative to an elongate axis of the housing of the tilt drive 230 would be prohibited, the control subsystem 500 of the head unit microscope assembly 20 would send a signal to actuate the alarm module 32 of the foot control assembly 30. In this example, the actuated alarm module 32 would act to inform the surgeon that they have reached the limit of the rotational movement of the drive member relative to an elongate axis of the housing of the tilt drive 230.

In yet another optional aspect, if the positional sensor 296 of the focus drive 270 senses that the operational movement of the focus drive 270 is approaching or has reached a range of movement limitation of the focus drive 270, such that further axial movement of the focus drive 270 would be prohibited along the focus drive axis, the control subsystem 500 of the head unit microscope assembly 20 would send a signal to actuate the alarm module 32 of the foot control assembly 30. In this example, the actuated alarm module 32 would act to inform the surgeon that they have reached the limit of the range of movement of the focus drive 270 along its axis of movement.

It is contemplated that the range of movement limitations for the respective XY directional stage 220, tilt drive 230, and/or the focus drive 270 can be selectively set in the control subsystem 500. Optionally, the range of movement limitations for the respective XY directional stage 220, tilt drive 230, and/or the focus drive 270 can be pre-set in the control subsystem 500. It is further contemplated that the operator can instruct the control subsystem 500 to not actuate the alarm module 32 of the foot control assembly 30 if an end of excursion limitation is reached in any or respective ones of the XY directional stage 220, the tilt drive 230, and/or the focus drive 270.

As described herein in various optional embodiments, if any of the XY directional stage 220, tilt drive 230, and/or the focus drive 270 has end limit detection as previously mentioned, and if the previously described light illumination controls have end limits as well, such as an off to full illumination to off function, it is feasible to have audible and tactile feedback to the user when an end-limit is reached—such feedback can be selectively tied to particular movement functions or can be provided for any or all of the movement functions described. In this aspect, when a "limit" is reached for a particular movement function, a vibratory motor in the foot control assembly 30 could give feedback to the user that an end-limit has been reached as the physician is attempting try to drive the function beyond the respective "end of excursion" limitation. Optionally, an audible beep or tome could also be provided to give feedback to the user that an end-limit has been reached as the physician is attempting try to drive the function beyond the respective "end of excursion" limitation. The vibratory and or audible warning feature allows the physician to receive the necessary "end of excursion" limitation feedback without having to look up from the microscope.

As shown in FIG. 31, it is contemplated that the alarm module 32 can comprise at least one of an audible alarm module 33, which is configured to provide an audible alarm notice to the user upon actuation, and/or a tactile alarm module 34, which is configured to provide a tactile alarm notice to the user, such as the exemplified vibrational alarm, upon actuation.

It is further contemplated that the alarm module can provide different tactile and/or sound indication to the operator depending upon which of the respective XY directional stage 220, tilt drive 230, and/or the focus drive 270 has triggered the control subsystem 500 to actuate the alarm module 32. This, in this exemplary aspect, one will appreciate that the operator can intuit which respective end of excursion limitation has been reached by the generated sound/feel of the alarm module 32.

In addition to a conventional power switch and because the foot control assembly 30 can be configured to be battery operated for wireless functionality, it is contemplated that the foot control assembly 30 can be configured to selectively switch to a low power standby mode and/or a power off mode when not in operation to preserve power. In this aspect, the foot control assembly 30 can be configured to switch to the low power standby mode and/or the power off mode when a desired inactivity time limit has elapsed in which none of the conventional control switches of the foot control assembly 30 has been actuated. For example, if none of the control switches of the foot control assembly 30 was actuated for a system selected period of inactivity, or an operator selected period of inactivity, the foot control assembly 30 would switch to the low power standby mode and/or the power off mode.

As shown in FIG. 19, it is optionally contemplated that the foot control assembly 30 can comprise at least one shock sensor module 36 that is configured to allow the operator to move the foot control assembly 30 to a powered-up mode from either the low power standby mode and/or the power off mode by simply moving or otherwise jarring the foot control assembly. It this aspect, the shock sensor module 36 can comprise a magnet mounted distally on a spring that is circumferentially surrounded by, and spaced from, a coil. One skilled in the art will appreciate, when the foot control assembly 30 is kicked or otherwise bumped by the operator, the magnet moves inside the coil and induces a current in the coil. Circuitry in the shock sensor module 36 of the foot control assembly 30 evaluates this voltage, and if it exceeds an adjustable voltage threshold, it will trigger a wake-up procedure for the foot control assembly 30.

In operation, the foot control assembly 30 can be configured to automatically switch to a sleep mode after a predetermined period of inactivity to conserve battery life. The predetermined period of inactivity, for example and without limitation, 10 minutes, 20 minutes, 30 minutes, etc., can selectively be inputted by the operator into the system or can be preprogramed into the system. As described above, when the shock sensor module 36 detects a sharp vibration (light kick or tap) to the foot control assembly, the foot control assembly 30 reactivates and returns to normal function.

In operation, the shock sensor module 36 is configured to allow for the foot control assembly 30 to sit at various angles during storage and not cause false triggers, and it allows a sensitivity adjustment so slight vibrations won't trigger a false wake-up In optional aspects, as shown in FIG. 21, the foot control assembly 30 can be configured to bind to a specific head unit microscope assembly so that multiple head unit microscope assembly systems can operate in near vicinity and not crosstalk. Further, the foot control assembly can be configured to be connected to the head unit microscope assembly by cable in case of radio interference, battery failure, or communications failure.

Floor Stand Assembly

The floor stand assembly 40 can be used if the user does not have a current upgradable floor stand or wants added features that are provided by the floor stand assembly. The floor stand assembly 40 is configured to be light weight, when compared to existing surgical operating microscopes, which allows for easier movement of the floor stand and the coupled head unit microscope assembly by the user. To stabilize the floor stand assembly, the bottom portion of the floor stand is configured to accept the mounting of conventional weight plates, which allows the selective addition of the required ballast to insure the desired positional stability of the surgical microscope system. In various optional aspects, the floor stand assembly further can include caster wheels for aiding in positioning the floor stand is the desired position and/or magnetic brakes to allow for locking of the floor stand in the desired position. In a further aspect, the floor stand assembly can include a bias element 43, such as, for example and without limitation, a pneumatic spring, a coil spring, and the like, for assisting in the positioning of the arm member of the floor stand. In the exemplary aspect, and as shown in FIG. 1 and FIG. 2, the distal portion 44 of the arm member 42 is configured to receive the mounting adaptor of the head unit microscope assembly.

Head Rest Assembly

The headrest assembly 60 is attachable to the head unit microscope assembly and is configured to support the head, neck and back of a user who leans against it, and the invention provides a selectable position against which the user may lean in order to prevent neck and back strain. An example of an exemplary headrest assembly 60 is disclosed in U.S. Pat. No. 9,772,497, the entire contents of which are hereby incorporated by reference.

Figure 35:
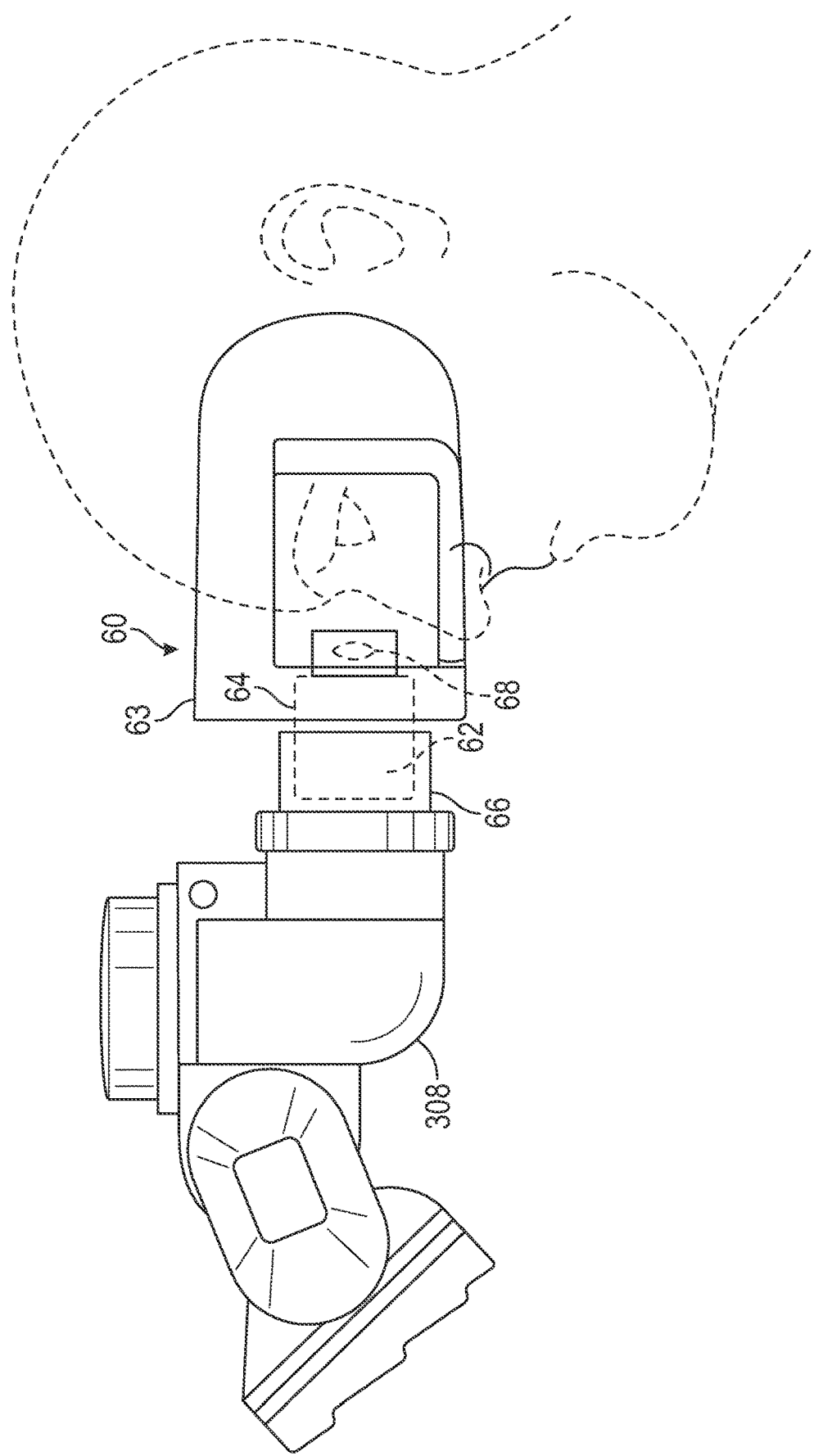
FIG. 35 schematically illustrates an example of a headrest assembly showing a partially transparent side view showing eyepieces secured to a binocular optics module of the microscope subassembly.

Referring to FIG. 35, the headrest assembly 60 is configured to be conventionally mountable to the binocular optics module 308 of the microscope subassembly 300. In one aspect, the headrest assembly 60 can include preset values obtained from measurements of the user's face in order to minimize practical difficulties in using adjustable settings and also to reduce or eliminate strain to the neck and back of the user. In one aspect, the headrest assembly 60 can include two eyepieces 62 that are connected to a mask 63 that defines a pair of eyepiece openings 64. Optionally, the mask 63 can be formed to complement the face structure of the user. As shown, each eyepiece 62 can include at least one rigid sidewall and at least one optical element for transmitting light beams from the optical device to the user's eye.

In the disclosed aspect, each eyepiece also has a first end 66 and a second end 67. In this aspect, the first end of each eyepiece can be configured for attachment to a portion of the binocular optics module 308 of the microscope subassembly 300 and the second end of each eyepiece is mounted to the mask 65. As shown, each eyepiece also includes a lens 68 that is positioned proximate the second end 67. Wherein a defined center of each lens 68 is spaced in relation to the center of the other said lens at a distance similar to a measured pupillary distance (PD) of the user and is also positioned at a desired eye relief distance, such that the user can rest their face against the mask and thereby prevent neck and back strain.

References are made to block diagrams of systems, methods, apparatuses, and computer program products according to example embodiments. It will be understood that at least some of the blocks of the block diagrams, and combinations of blocks in the block diagrams, may be implemented at least partially by computer program instructions. These computer program instructions may be loaded onto a general-purpose computer, special purpose computer, special purpose hardware-based computer, or other programmable data processing apparatus to produce a machine, such that the instructions which execute on the computer or other programmable data processing apparatus create means for implementing the functionality of at least some of the blocks of the block diagrams, or combinations of blocks in the block diagrams discussed.

These computer program instructions may also be stored in a non-transitory computer-readable memory that can direct a computer or other programmable data processing apparatus to function in a particular manner, such that the instructions stored in the computer-readable memory produce an article of manufacture including instruction means that implement the function specified in the block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide task, acts, actions, or operations for implementing the functions specified in the block or blocks.

One or more components of the systems and one or more elements of the methods described herein may be implemented through an application program running on an operating system of a computer. They may also be practiced with other computer system configurations, including hand-held devices, multiprocessor systems, microprocessor-based or programmable consumer electronics, mini-computers, mainframe computers, and the like.

Application programs that are components of the systems and methods described herein may include routines, programs, components, data structures, etc. that may implement certain abstract data types and perform certain tasks or actions. In a distributed computing environment, the application program (in whole or in part) may be located in local memory or in other storage. In addition, or alternatively, the application program (in whole or in part) may be located in remote memory or in storage to allow for circumstances where tasks can be performed by remote processing devices linked through a communications network.

Although only a few exemplary embodiments have been described in detail herein, those skilled in the art will readily appreciate that many modifications are possible in the exemplary embodiments without materially departing from the novel teachings and advantages of the embodiments of the present disclosure. Accordingly, all such modifications are intended to be included within the scope of the embodiments of the present disclosure as defined in the following claims.

We claim:

1. A surgical microscope system, comprising: a processing system, wherein an at least one memory of the processing system is configured to store program instructions; an illumination system comprising: a plurality of light sources configured for illumination of targeted tissue area of a patient, the plurality of light sources comprising a coaxial light source and a pair of oblique light sources that are configured to illuminate the targeted tissue area at a selected light intensity level, wherein the coaxial light source forms a beam of divergent light that is configured to provide a wide dispersion of light energy on the targeted tissue area, wherein each of the plurality of light sources comprises a large light emitting surface (LES) that has an illumination area of greater than about 20.0 mm$^2$, wherein the at least one memory of the processing system is configured to store program instructions that when executed cause the intensity of light energy incident on the targeted tissue area provided by the plurality of light sources to be selectively configured such that the ratio of light between the coaxial light source and the pair of oblique light sources are maintained at a user preference light ratio level setting, wherein a color-rendering index of at least one of the plurality of light sources is at least 70, wherein each of the plurality of light sources is configured to generate a peak percentage level of normalized radiant power having radiation with wavelengths between about 600 and 700 nm, and wherein each of the plurality of light sources is configured to generate a color temperature of that is less than about 4500K.

2. The surgical microscope system of claim 1, wherein the color-rendering index of at least one of the plurality of light sources is at least 90.

3. The surgical microscope system of claim 1, wherein the color-rendering index of at least one of the plurality of light sources is between 95 and 99.9.

4. The surgical microscope system of claim 1, wherein the color-rendering index of each of the plurality of light sources is at least 70.

5. The surgical microscope system of claim 1, wherein the color-rendering index of each of the plurality of light sources is at least 90.

6. The surgical microscope system of claim 1, wherein the color-rendering index of each of the plurality of light sources is between 95 and 99.9.

7. The surgical microscope system of claim 1, wherein each of the plurality of light sources are configured to generate a peak percentage level of normalized radiant power having radiation with wavelengths of about 650 nm.

8. The surgical microscope system of claim 1, wherein each of the plurality of light sources is configured to generate a color temperature that is less than about 3800K.

9. The surgical microscope system of claim 1, wherein each of the plurality of light sources is configured to generate a color temperature that is between 3100K and 3900K.

10. The surgical microscope system of claim 1, wherein each of the plurality of light sources is configured to generate a color temperature that is between 3300K and 3600K.

11. The surgical microscope system of claim 1, wherein the at least one memory of the processing system is configured to store program instructions that when executed adjust the spectral makeup of the total light generated by the coaxial light source and the pair of oblique light sources to a desired spectrum of incident light in order to obtain a level of desired red reflex from the light illumination incident on an eye of the patient.

12. The surgical microscope system of claim 1, wherein the at least one memory of the processing system is configured to store program instructions that when executed adjust the color temperature of the total light generated by the coaxial light source and the pair of oblique light sources to a desired color temperature level of incident light in order to obtain a level of desired red reflex from the light illumination incident on an eye of the patient.

13. The surgical microscope system of claim 1, wherein the beam of divergent light emitted by the coaxial light source is centered between the user's left and right optical pathways.

14. The surgical microscope system of claim 1, wherein the wide dispersion of light energy on a retina of a patient retina allows for more of an interior region of the eye to be illuminated while providing for evenly dispersed light energy across the targeted tissue area.

15. The surgical microscope system of claim 14, wherein light generated by the coaxial light source is configured to fill the targeted tissue area at a focal plane.

16. The surgical microscope system of claim 1, wherein the beam of divergent light is configured to be selectively decreased in diameter without increasing the intensity of the light energy incident on the targeted tissue area.

17. The surgical microscope system of claim 1, wherein the pair of oblique light sources emit oblique beams that are angled at a desired angle of incidence β between about 5 to 15 degrees, relative to an optical axis.

18. The surgical microscope system of claim 1, wherein the pair of oblique light sources are positioned on opposite sides of the coaxial light source.

19. The surgical microscope system of claim 1, wherein the illumination area of each large LES is greater than about 30.0 mm$^2$.

20. The surgical microscope system of claim 1, wherein the illumination area of each large LES is greater than about 35.0 mm$^2$.

21. The surgical microscope system of claim 1, wherein a total illumination area of the large light emitting surfaces of the coaxial light source and the pair of oblique light sources is between about 80 to about 140 mm$^2$.

22. A surgical microscope system, comprising: a processing system, wherein an at least one memory of the processing system is configured to store program instructions; an illumination system comprising: a plurality of light sources configured for illumination of targeted tissue area of a patient, the plurality of light sources comprising a coaxial light source and a pair of oblique light sources that are configured to illuminate the targeted tissue area at a selected light intensity level, wherein the coaxial light source forms a beam of divergent light that is configured to provide a wide dispersion of light energy on the targeted tissue area; wherein the at least one memory of the processing system is configured to store program instructions that when executed adjust the spectral makeup of the total light generated by the coaxial light source and the pair of oblique light sources to a desired spectrum of incident light in order to obtain a level of desired red reflex from the light illumination incident on an eye of the patient, wherein a color-rendering index of at least one of the plurality of light sources is at least 70, wherein each of the plurality of light sources is configured to generate a peak percentage level of normalized radiant power having radiation with wavelengths between about 600 and 700 nm, and wherein each of the plurality of light sources is configured to generate a color temperature of that is less than about 4500K.

23. The surgical microscope system of claim 22, wherein the at least one memory of the processing system is configured to store program instructions that when executed cause the intensity of light provided by the plurality of light sources to be selectively configured such that the ratio of light between the coaxial light source and the pair of oblique light sources are maintained at a user preference light ratio level setting.

24. The surgical microscope system of claim 22, wherein the at least one memory of the processing system is configured to store program instructions that when executed adjust the color temperature of the total light generated by the coaxial light source and the pair of oblique light sources to a desired color temperature level of incident light in order to obtain a level of desired red reflex from the light illumination incident on an eye of the patient.

25. A surgical microscope system, comprising: a processing system, wherein an at least one memory of the processing system is configured to store program instructions; an illumination system comprising: a plurality of light sources configured for illumination of targeted tissue area of a patient, the plurality of light sources comprising a coaxial light source and a pair of oblique light sources that are configured to illuminate the targeted tissue area at a selected light intensity level, wherein the coaxial light source forms a beam of divergent light that is configured to provide a wide dispersion of light energy on the targeted tissue area, wherein each of the plurality of light sources comprises a large light emitting surface (LES) that has an illumination area of greater than about 30.0 mm$^2$, wherein the at least one memory of the processing system is configured to store program instructions that when executed adjust the spectral makeup of the total light generated by the coaxial light source and the pair of oblique light sources to a desired spectrum of incident light in order to obtain a level of desired red reflex from the light illumination incident on an eye of the patient.

26. The surgical microscope system of claim 25, wherein the color-rendering index of at least one of the plurality of light sources is at least 70.

27. The surgical microscope system of claim 25, wherein each of the plurality of light sources is configured to generate a peak percentage level of normalized radiant power having radiation with wavelengths between about 600 and 700 nm.

28. The surgical microscope system of claim 25, wherein each of the plurality of light sources is configured to generate a color temperature of that is less than about 4500K.

29. The surgical microscope system of claim 25, wherein the at least one memory of the processing system is configured to store program instructions that when executed cause the intensity of light provided by the plurality of light sources to be selectively configured such that the ratio of light between the coaxial light source and the pair of oblique light sources are maintained at a user preference light ratio level setting.

30. The surgical microscope system of claim 28, wherein the at least one memory of the processing system is configured to store program instructions that when executed adjust the color temperature of the total light generated by the coaxial light source and the pair of oblique light sources to a desired color temperature level of incident light in order to obtain a level of desired red reflex from the light illumination incident on an eye of the patient.

31. A surgical microscope system, comprising: a head unit microscope assembly comprising: a processing system, wherein an at least one memory of the processing system is configured to store program instructions; an illumination system comprising: a plurality of light sources configured for illumination of targeted tissue area of a patient, the plurality of light sources comprising a coaxial light source and a pair of oblique light source that are configured to illuminate the targeted tissue area at a selected light intensity level, wherein the coaxial light source forms a beam of divergent light that is configured to provide a wide dispersion of light energy on the targeted tissue area, wherein each of the plurality of light sources comprises a large light emitting surface (LES) that has an illumination area of greater than about 30.0 mm$^2$, a foot control assembly in operative communication with the head unit microscope assembly; and a floor stand configured to support the head unit microscope assembly in a desired operative position, wherein the at least one memory of the processing system is configured to store program instructions that when executed adjust the spectral makeup of the total light generated by the coaxial light source and the pair of oblique light sources to a desired spectrum of incident light in order to obtain a level of desired red reflex from the light illumination incident on an eye of the patient.

* * * * *